United States Patent
Fish et al.

(10) Patent No.: US 12,235,233 B2
(45) Date of Patent: *Feb. 25, 2025

(54) CURRENT MEASUREMENT APPARATUS, MOLECULAR ENTITY SENSING APPARATUS, METHOD OF MEASURING A CURRENT, METHOD OF SENSING A MOLECULAR ENTITY

(71) Applicant: Oxford Nanopore Technologies PLC, Oxford (GB)

(72) Inventors: David A. Fish, AE Eindhoven (NL); Hugo Veenstra, AE Eindhoven (NL); Emil Totey, AE Eindhoven (NL)

(73) Assignee: Oxford Nanopore Technologies PLC, Oxford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/643,194

(22) Filed: Apr. 23, 2024

(65) Prior Publication Data
US 2024/0393282 A1 Nov. 28, 2024

Related U.S. Application Data

(63) Continuation of application No. 17/440,222, filed as application No. PCT/GB2020/050248 on Feb. 4, 2020, now Pat. No. 11,994,486.

(30) Foreign Application Priority Data
Mar. 19, 2019 (GB) .................. 1903742.3

(51) Int. Cl.
*G01N 27/12* (2006.01)
*G01N 33/487* (2006.01)

(52) U.S. Cl.
CPC ..... *G01N 27/128* (2013.01); *G01N 33/48721* (2013.01)

(58) Field of Classification Search
CPC ........... G01N 27/128; G01N 33/48721; G01N 27/228; G01R 19/0023; G01R 19/0061;
(Continued)

(56) References Cited

U.S. PATENT DOCUMENTS

| 11,994,486 B2 | 5/2024 | Fish et al. |
| 2013/0048499 A1 | 2/2013 | Mayer et al. |

(Continued)

FOREIGN PATENT DOCUMENTS

| CN | 204575228 U | 8/2015 |
| CN | 107144719 A | 9/2017 |

(Continued)

OTHER PUBLICATIONS

International Search Report and Written Opinion mailed May 12, 2020 for International Application No. PCT/GB2020/050248.
(Continued)

*Primary Examiner* — Jermele M Hollington
*Assistant Examiner* — Zannatul Ferdous
(74) *Attorney, Agent, or Firm* — Wolf, Greenfield & Sacks, P.C.

(57) ABSTRACT

Methods and apparatus for measuring current are provided. In one arrangement, a first charge amplifier integrates a current to be measured. A processing circuit filters an output from the first charge amplifier using a first low pass filter module and a second low pass filter module. A second charge amplifier integrates a current derived from the filtered output from the first charge amplifier. The apparatus is configured to reset the first charge amplifier at the start of each of a plurality of sensing frames. The processing circuit obtains at least a first sample of the output from the first charge amplifier in each sensing frame. The sampling of the first sample alternates from one sensing frame to the next
(Continued)

sensing frame between sampling via the first low pass filter module and sampling via the second low pass filter module.

16 Claims, 19 Drawing Sheets

(58) Field of Classification Search
CPC . G01R 19/0053; G01R 15/00; G01R 19/0046
See application file for complete search history.

(56) References Cited

U.S. PATENT DOCUMENTS

| | | | |
|---|---|---|---|
| 2015/0001097 A1 | 1/2015 | Malecha | |
| 2015/0265994 A1 | 9/2015 | Hyde et al. | |
| 2016/0100116 A1 | 4/2016 | Mesgarini et al. | |
| 2018/0039809 A1* | 2/2018 | Chung | G06V 40/1324 |
| 2018/0143178 A1* | 5/2018 | Fish | G01N 33/48728 |
| 2022/0326832 A1* | 10/2022 | Lee | G06F 3/044 |

FOREIGN PATENT DOCUMENTS

| | | | |
|---|---|---|---|
| DE | 299839 A5 | 5/1992 | |
| EP | 2698989 A2 | 2/2014 | |
| EP | 3546956 A1 | 10/2019 | |
| KR | 20180078603 A | 7/2018 | |
| WO | 2000/28312 A1 | 5/2000 | |
| WO | 2003/050547 A2 | 6/2003 | |
| WO | WO 2006/100484 A2 | 9/2006 | |
| WO | WO 2008/102120 A1 | 8/2008 | |
| WO | WO 2008/102121 A1 | 8/2008 | |
| WO | WO 2009/035647 A1 | 3/2009 | |
| WO | WO 2009/077734 A2 | 6/2009 | |
| WO | WO 2010/122293 A1 | 10/2010 | |
| WO | WO 2011/067559 A1 | 6/2011 | |
| WO | WO 2013/153359 A1 | 10/2013 | |
| WO | WO 2014/064443 A1 | 5/2014 | |
| WO | WO 2014/064444 A1 | 5/2014 | |
| WO | WO 2014/064449 A1 | 5/2014 | |
| WO | WO 2014/066909 A1 | 5/2014 | |
| WO | WO 2016/034591 A2 | 3/2016 | |
| WO | WO 2016/059427 A1 | 4/2016 | |
| WO | WO 2016/181118 A1 | 11/2016 | |

OTHER PUBLICATIONS

International Preliminary Report on Patentability mailed Sep. 30, 2021 for International Application No. PCT/GB2020/050248.

Gonzalez-Perez et al., Biomimetic triblock copolymer membrane arrays: a stable template for functional membrane proteins. Langmuir. Sep. 15, 2009;25(18):10447-50. doi: 10.1021/la902417m.

Langecker et al., Synthetic lipid membrane channels formed by designed DNA nanostructures. Science. Nov. 16, 2012;338(6109):932-6. doi: 10.1126/science.1225624.

Lieberman et al., Processive replication of single DNA molecules in a nanopore catalyzed by phi29 DNA polymerase. J Am Chem Soc. Dec. 22, 2010;132(50):17961-72. doi: 10.1021/ja1087612. Epub Dec. 1, 2010. Author Manuscript, 21 pages.

Montal et al., Formation of bimolecular membranes from lipid monolayers and a study of their electrical properties. Proc Natl Acad Sci U S A. Dec. 1972;69(12):3561-6. doi: 10.1073/pnas.69.12.3561.

Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.

Yusko et al., Controlling protein translocation through nanopores with bio-inspired fluid walls. Nat Nanotechnol. Apr. 2011;6(4):253-60. doi: 10.1038/nnano.2011.12. Epub Feb. 20, 2011. Author Manuscript, 22 pages.

* cited by examiner

CURRENT MEASUREMENT APPARATUS, MOLECULAR ENTITY SENSING APPARATUS, METHOD OF MEASURING A CURRENT, METHOD OF SENSING A MOLECULAR ENTITY

RELATED APPLICATIONS

This application is a continuation of U.S. patent application Ser. No. 17/440,222, filed Sep. 17, 2021, which is a national stage filing under 35 U.S.C. § 371 of international application number PCT/GB2020/050248, filed Feb. 4, 2020, which claims the benefit of Great Britain application number GB 1903742.3, filed Mar. 19, 2019. The entirety of the applications listed above is herein incorporated by reference.

The invention relates to measuring small electrical currents with high sensitivity, particularly but not exclusively in the context of sensing molecular entities, for example via interactions between the molecular entities and a nanopore sensor.

It is known to sense molecular entities using a nanopore sensor comprising a membrane protein inserted in an amphiphilic membrane. Interactions between the molecular entities and the membrane protein can cause characteristic modulations of an electrical signal appearing across the amphiphilic membrane. For example, an ionic current flowing through a membrane protein that is a protein pore can be modulated by the interactions. By monitoring an electrical signal appearing across the amphiphilic membrane it is possible to detect the characteristic modulations and thereby sense the molecular entities. A variety of technologies have been proposed based on this principle, one example being disclosed in WO-2008/102120.

Sensing of molecular entities using a nanopore sensor provides a method of identifying single molecules and molecular entities. There are a wide range of possible applications, such as sequencing of DNA or other nucleic acids; sensing of chemical or biological molecules for security and defence; detection of biological markers for diagnostics; ion channel screening for drug development; and label free analysis of interactions between biological molecules.

The currents that are detected are typically in the range of 20 pA to 100 pA for DNA sequencing and with an open pore the currents are in the range of 50 pA to 500 pA. The electronic detection of such currents is challenging. A multi-channel device may be employed in conjunction with an array of sensors. The device may be implemented using Application Specific Integrated Circuits (ASICs).

Sensitive current measurements are also required in other applications. For example, medical X-ray detectors are known in which charge created by X-ray quanta in direct and indirect conversion materials is detected. Such detectors also typically use ASICs and the minimum charge detection levels may be around 10000 electrons with about 1000 electrons of RMS noise. The X-ray detectors may operate by accumulating charge on a capacitance. The charge may be accumulated over a period of milliseconds for example. The accumulated charge may be read out into a charge amplifier in a few micro-seconds. In configurations of this type current levels are therefore in the nanoampere region. X-ray detectors employing thousands of sensing channels are known.

The charge levels seen in known nanopore sequencing applications are similar to those seen in known X-ray detectors. Similar noise levels are also required, typically equivalent to about 2 pA RMS current noise at 10 kHz sampling. FIG. 1 shows an example current measurement apparatus configured to measure a current flowing through a nanopore. Corresponding arrangements, adapted as appropriate, maybe provided for use in medical X-ray detectors or in other charge or current measurement devices.

The example apparatus comprises a charge integrating amplifier 102 (which may also be referred to as a charge amplifier) which acts to integrate charge flowing through a nanopore represented by a resistor 101. A 50 pA current will generate a voltage of about 50 mV over 100 µs with the component values shown in the figure. After 100 µs the circuit is reset with a switch (not shown) on the integrating capacitance (the 100 fF capacitance in FIG. 1). FIG. 2 shows schematically how the voltage output rises as a function of time during the integration process.

The intrinsic noise performance can be analysed approximately as follows. FIG. 3 shows main noise sources in the apparatus of FIG. 1. The resistor $R_{PORE}$ (having resistance $R_{PORE}$) represents the resistance of the nanopore. Noise in the resistor is represented by $V_{NPORE}$. $R_{PORE}$ will typically be in the range of 3G to 20 GOhms or higher and will produce white noise $V_{NPORE}$ proportional to $\sqrt{4 k_B T R_{PORE}}$, where $k_B$ is Boltzmann's constant and T is temperature. The amplifier noise source is shown as $V_{NAMP}$ and will typically be around 1 µV/√Hz at 1 Hz down to the white noise floor of 3 nV/√Hz above 100 kHz for a CMOS integrated amplifier. An important component is the capacitance of the amphiphilic membrane (which may be a bi-lipid layer), marked as $C_{BL}$. $C_{BL}$ is relatively large, typically around 30 pF for example. Finally, the electrode resistance $R_{ELE}$ and associated noise $V_{NELE}$ are marked. $R_{ELE}$ may typically have a value of around 4 kOhms.

Although the nanopore resistance $R_{PORE}$ is very high it is heavily filtered by the capacitance $C_{BL}$ and its contribution to the overall RMS noise is negligible except at very low frequencies. The amplifier noise $V_{NAMP}$ and the electrode resistance noise $V_{NELE}$ are the dominant contributions because they are amplified by the ratio of the capacitance $C_{BL}$ to the capacitance $C_{FB}$ of the integrating capacitor. Typically this ratio is about 300. The RMS current noise under these conditions is about 5 pA RMS, which is relatively high. The RMS current noise can be reduced by applying known filtering techniques. For example, by applying correlated double sampling (CDS) and low pass (LP) filtering to the arrangement of FIG. 3 it is possible to reduce the noise level down to about 1.4 pA, which is acceptable for many applications, including detecting biological molecules in nanopores. The correlated double sampling has the effect of a high pass filter, so the combination is a band-pass filter at the sampling rate (or integration period) of the circuit.

Known circuitry, especially sensing circuits or those used to implement the noise reduction techniques discussed above can undesirably increase power consumption and require additional heat dissipation. This may limit practical applications, particularly where large arrays of the circuitry are needed to provide high throughput and/or where implementation is desired in a small and/or battery-powered device.

It is an object of the invention to at least partially address one or more of the problems discussed above.

According to an aspect, there is provided a current measuring apparatus comprising: a first charge amplifier configured to integrate a current to be measured; a processing circuit configured to filter an output from the first charge amplifier using a first low pass filter module and a second low pass filter module; and a second charge amplifier configured to integrate a current derived from the filtered output from the first charge amplifier, wherein: the apparatus is configured to reset the first charge amplifier at the start of each of a plurality of sensing frames; the processing circuit is configured to obtain at least a first sample of the output from the first charge amplifier in each sensing frame; and the sampling of the first sample alternates from one sensing frame to the next sensing frame between sampling via the first low pass filter module and sampling via the second low pass filter module.

The alternating of sampling from one sensing frame to the next sensing frame avoids the need for a buffer, thereby allowing the circuitry to be implemented with fewer amplifiers. This facilitates power saving and/or limits heat dissipation without compromising noise suppression performance.

In an embodiment, the first low pass filter module comprises a first RC filter and the second low pass filter module comprises a second RC filter. In each sensing frame in which sampling of a first sample is not performed via the first low pass filter module, a first sample from a directly preceding sensing frame is stored as charge on a capacitance component of the first RC filter; and in each sensing frame in which sampling of the first sample is not performed via the second low pass filter module, a first sample from a directly preceding sensing frame is stored as charge on a capacitance component of the second RC filter. The capacitance component of the first RC filter comprises a first plurality of capacitors and in each sensing frame in which sampling of the first sample is performed via the first low pass filter module, a selected attenuation is applied to charge representing information about the current to be measured by sampling charge only from a selected subset of the first plurality of capacitors; and the capacitance component of the second RC filter comprises a second plurality of capacitors and in each sensing frame in which sampling of the first sample is performed via the second low pass filter module, a selected attenuation is applied to charge representing information about the current to be measured by sampling charge only from a selected subset of the second plurality of capacitors.

Thus, circuitry is provided allowing selective attenuation to be applied without requiring amplifiers or introducing additional sources of noise. This facilitates power saving and/or limits heat dissipation.

In an embodiment, the first sample and a second sample of the output from the first charge amplifier are obtained in each sensing frame and the processing circuit is configured to perform correlated double sampling using the first samples and second samples. The processing circuit further comprises at least one further low pass filter module; and the apparatus is configured to sample the second sample via the at least one further low pass filter module.

In an embodiment, the at least one further low pass filter module consists of one further low pass filter module; and the apparatus is configured such that the sampling of the second sample is performed exclusively via the further low pass filter module for all sensing frames.

Implementing correlated double sampling using only a single further low pass filter module reduces silicon area requirements relative to arrangements in which multiple separate further low pass filter modules are provided.

In an embodiment, each of the first low pass filter module, the second low pass filter module, and the further low pass filter module is reset in each sensing frame in which the respective low pass filter module obtains a sample. The resetting of each low pass filter module is performed by bypassing a resistance component of an RC filter of the low pass filter module. The timing of the resetting of each low pass filter module is such that each of the first sample and the second sample is obtained an equal time after the resetting of the low pass filter module via which the sample is sampled.

This approach means the first sample is obtained at exactly the same point during the settling of the low pass filter module as the second sample, which means that any effect from the settling is the same for both samples and cancels out when the difference between the samples is obtained as part of the correlated double sampling procedure.

In an embodiment, the at least one further low pass filter module comprises a third lowpass filter module and a fourth low pass filter module and the apparatus is configured such that the sampling of the second sample alternates from one sensing frame to the next sensing frame between sampling via the third low pass filter module and sampling via the fourth low pass filter module.

This approach allows correlated double sampling to be implemented using relatively simple circuit timing.

In an embodiment, the first charge amplifier is configured such that the integration of the current is performed simultaneously across a first capacitive element and a second capacitive element and the resetting of the first charge amplifier is performed by allowing a charge stored on the second capacitive element to flow onto and at least partially cancel a charge stored on the first capacitive element.

This charge balancing soft reset approach promotes reduction of low frequency noise such as that which might be produced by noise folding. The approach also allows integration of an input signal to be performed with minimal or no interruption, allowing the circuit to respond to events that occur during the reset period that would otherwise not be seen. Additionally, the approach can remove the need for correlated double sampling, thereby providing more time for the charge amplifier to settle (e.g. the whole of a sensing frame), which means amplifier bandwidth and bias current can be reduced, thereby reducing power consumption.

According to an aspect, there is provided a current measuring apparatus comprising: a first charge amplifier configured to integrate a current to be measured; a processing circuit configured to filter an output from the first charge amplifier; and a second charge amplifier configured to integrate a current derived from the filtered output from the first charge amplifier, wherein: the first charge amplifier is configured such that the integration of the current is performed simultaneously across a first capacitive element and a second capacitive element and the resetting of the first charge amplifier is performed by allowing a charge stored on the second capacitive element to flow onto and at least partially cancel a charge stored on the first capacitive element.

According to an aspect, there is provided a current measuring apparatus comprising: a first charge amplifier configured to integrate a current to be measured; a processing circuit configured to filter an output from the first charge amplifier; and a second charge amplifier configured to integrate a current derived from the filtered output from the first charge amplifier, wherein: the processing circuit is configured such that information about the current to be measured propagates through the processing circuit from the first charge amplifier to the second charge amplifier as amounts of charge representing the current to be measured.

According to an aspect, there is provided a method of measuring current, comprising: using a first charge amplifier to integrate a current to be measured; filtering an output from the first charge amplifier using a first low pass filter module and a second low pass filter module; and using a second charge amplifier to integrate a current derived from the filtered output from the first charge amplifier, wherein: the first charge amplifier is reset at the start of each of a plurality of sensing frames; at least a first sample of the output from the first charge amplifier is obtained in each sensing frame; and the sampling of the first sample alternates from one sensing frame to the next sensing frame between sampling via the first low pass filter module and sampling via the second low pass filter module.

According to an aspect, there is provided a method of measuring current, comprising: using a first charge amplifier to integrate a current to be measured; filtering an output from the first charge amplifier; and using a second charge amplifier to integrate a current derived from the filtered output from the first charge amplifier, wherein: the integration of the current by the first charge amplifier is performed simultaneously across a first capacitive element and a second capacitive element and the resetting of the first charge amplifier is performed by allowing a charge stored on the second capacitive element to flow onto and at least partially cancel a charge stored on the first capacitive element.

According to an aspect, there is provided a method of measuring current, comprising: using a first charge amplifier to integrate a current to be measured; using a processing circuit to filter an output from the first charge amplifier; and using a second charge amplifier to integrate a current derived from the filtered output from the first charge amplifier, wherein: the processing circuit is configured such that information about the current to be measured propagates through the processing circuit from the first charge amplifier to the second charge amplifier as amounts of charge representing the current to be measured.

FIGS. 1 to 3 have already been described above. Embodiments of the invention will now be described, by way of example only, with reference to the remaining accompanying drawings in which corresponding reference symbols indicate corresponding parts, and in which:

Figure 1:
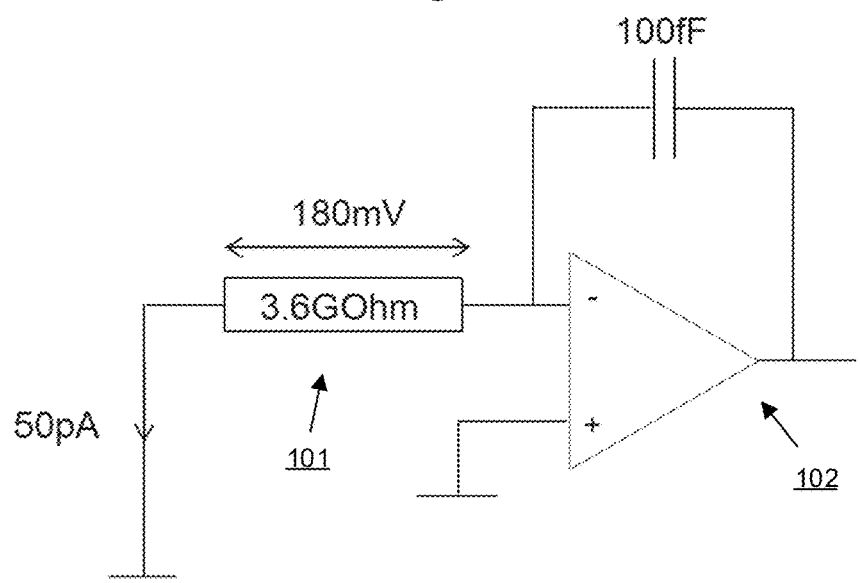
Figure 2:
Figure 3:
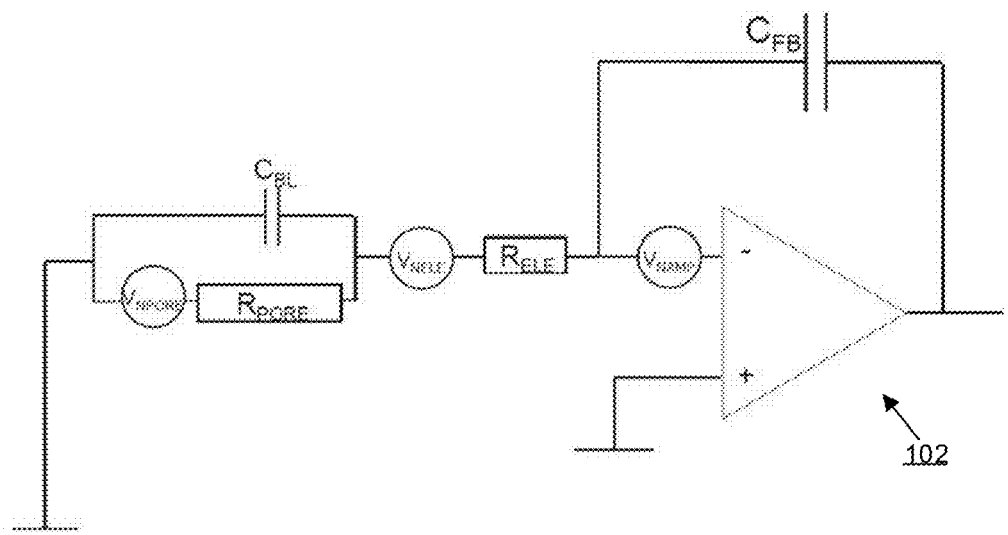
Figure 4:
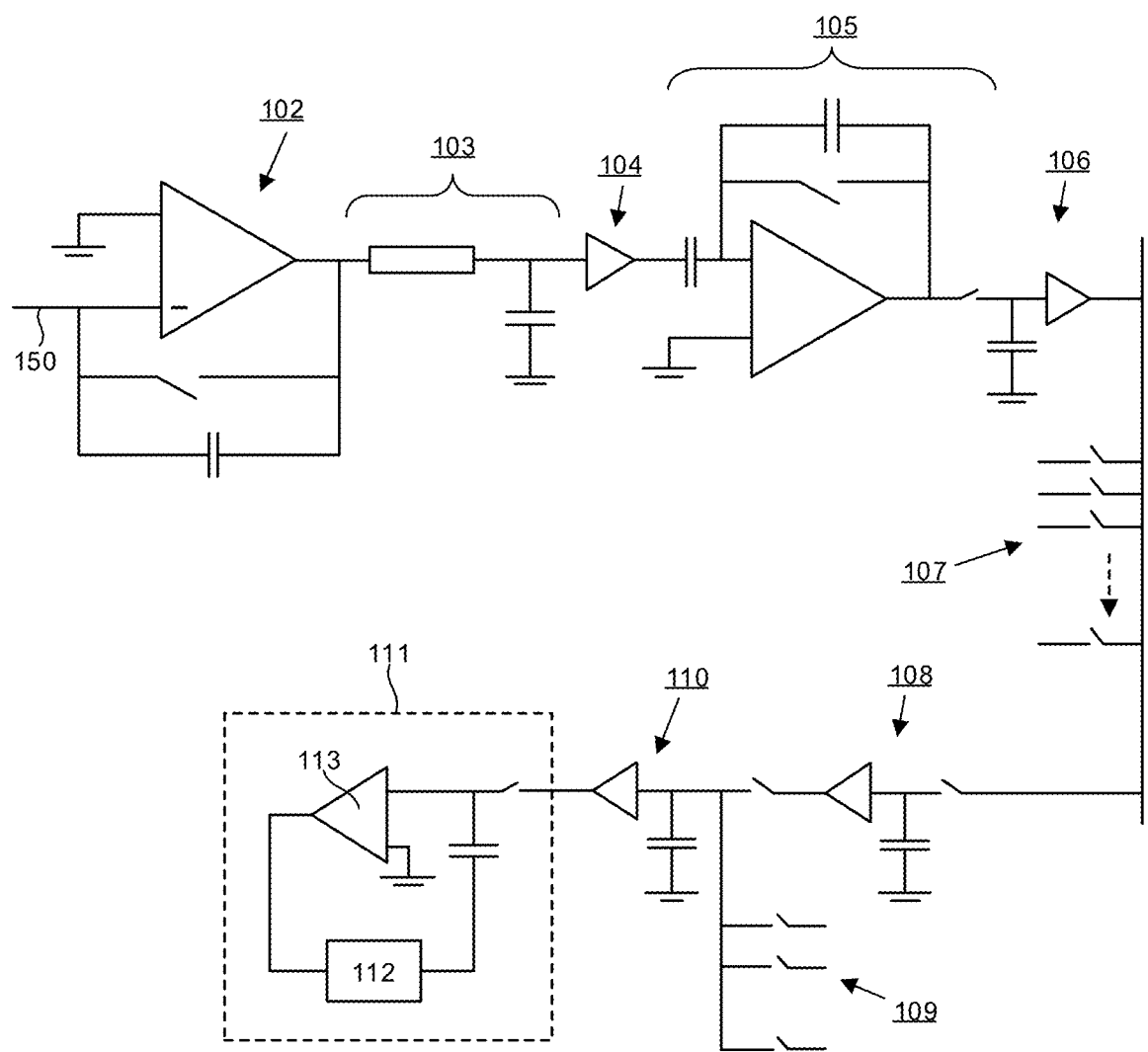
FIG. 4 depicts an example prior art signal processing chain for measuring a current using the circuit of FIG. 1.

FIG. 4 depicts an example prior art signal processing chain for measuring a current using the circuit of FIG. 1. The signal processing chain is configured to measure current in an array of units. Each unit may be referred to as a pixel. The pixels may be arranged in columns and rows. Noise reduction is implemented using correlated double sampling (CDS) and a low pass (LP) filter. The current to be measured is input at point 150 to a charge amplifier 102. The output from the charge amplifier 102 is input to an RC filter 103 (acting as a LP filter). An RC filter buffer 104 is provided between the charge amplifier 102 and a CDS amplifier with second stage gain 105. An output from the CDS amplifier with second stage gain 105 is input to a pixel sample and hold buffer 106. The pixel sample and hold buffer 106 temporarily stores an amount of charge representing the measured current until the pixel can be read out. A row multiplexing system 107 is provided for performing row multiplexing. An output from the row multiplexing system 107 is input to a column sample and hold buffer 108.

A column multiplexing system 109 is provided for performing column multiplexing. An output from the column multiplexing system 109 is input to an analog-to-digital converter (ADC) data buffer 110. An output from the ADC data buffer 110 is input to a Successive Approximation Register (SAR) ADC 111 (comprising a digital-to-analog converter (DAC) 112 and a comparator 113).

The arrangement of FIG. 4 comprises six amplifiers used in various configurations and a comparator (within the SAR ADC 111). Embodiments of the present disclosure reduce power consumption by providing arrangements which allow a current measurement apparatus 200 to be implemented with fewer amplifiers.

Figure 5:
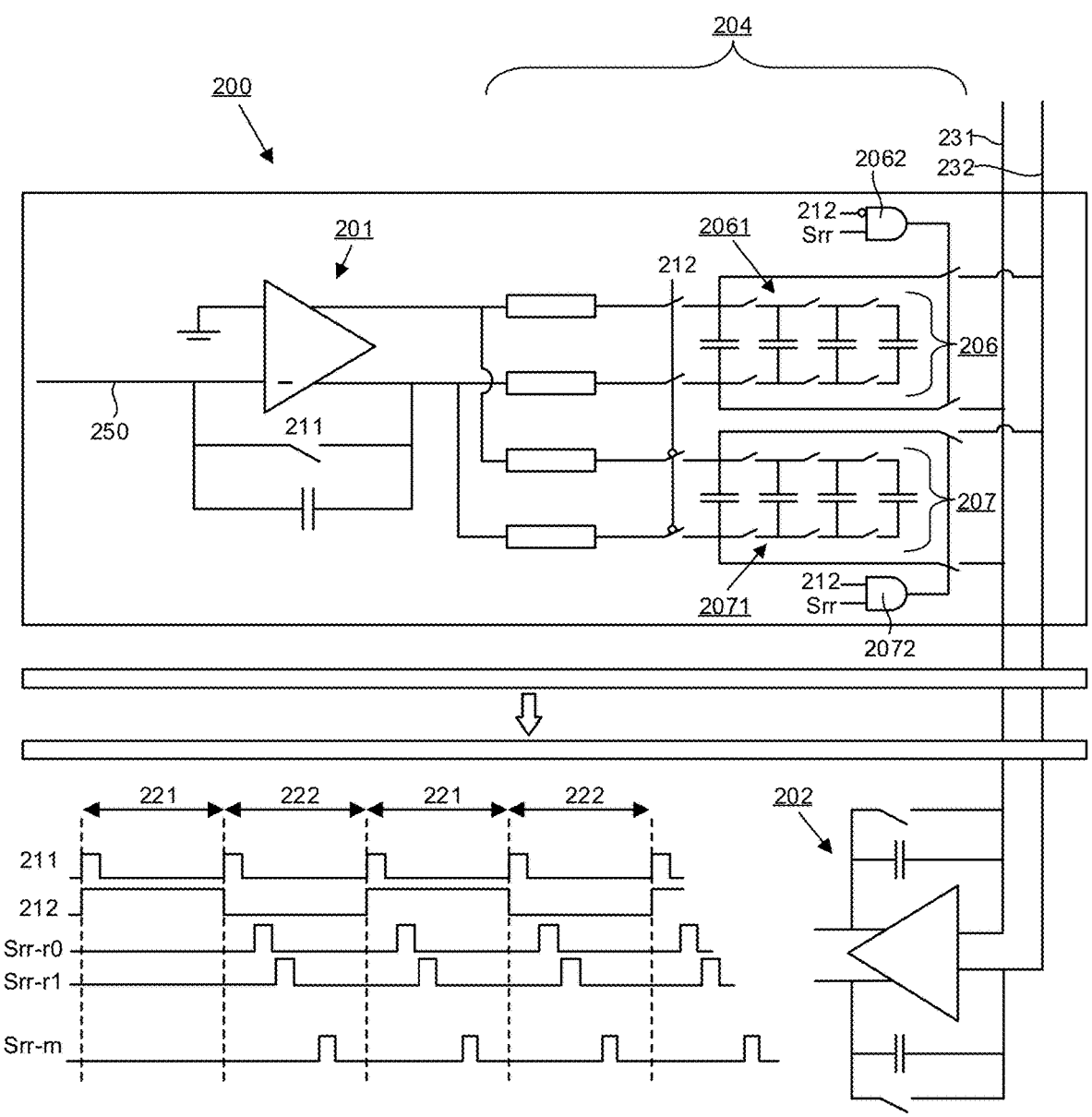
FIG. 5 depicts an example current measuring apparatus.

FIG. 5 depicts an example current measuring apparatus 200. The current measuring apparatus 200 comprises a first charge amplifier 201 configured to integrate a current to be measured (input at point 250). A processing circuit is provided that filters an output from the first charge amplifier 201. A second charge amplifier 202 integrates a current derived from the filtered output from the first charge amplifier 201.

The current measurement apparatus 200 reduces the number of amplifiers that are needed relative to the arrangement of FIG. 4 by replacing the RC filter 103 and RC filter buffer 104 with an amplifier-free low pass filter 204 which provides the same noise suppression performance without requiring any amplifier. Power consumption is therefore reduced.

In a class of embodiment, the strategy of avoiding use of amplifiers is extended to the whole signal path between the first charge amplifier 201 and the second charge amplifier 202. In such embodiments, the processing circuit is configured such that information about the current to be measured propagates through the processing circuit from the first charge amplifier 201 all the way to the second charge amplifier 202 as amounts of charge (optionally exclusively as amounts of charge) representing the current to be measured. This may be achieved by configuring the processing circuit (i.e. circuitry carrying the charge between the first charge amplifier 201 and the second charge amplifier 202) so that it consists exclusively of passive components and externally controllable switches. The embodiments below describe various techniques for implementing this strategy efficiently and with minimal silicon area requirements.

Figure 6:
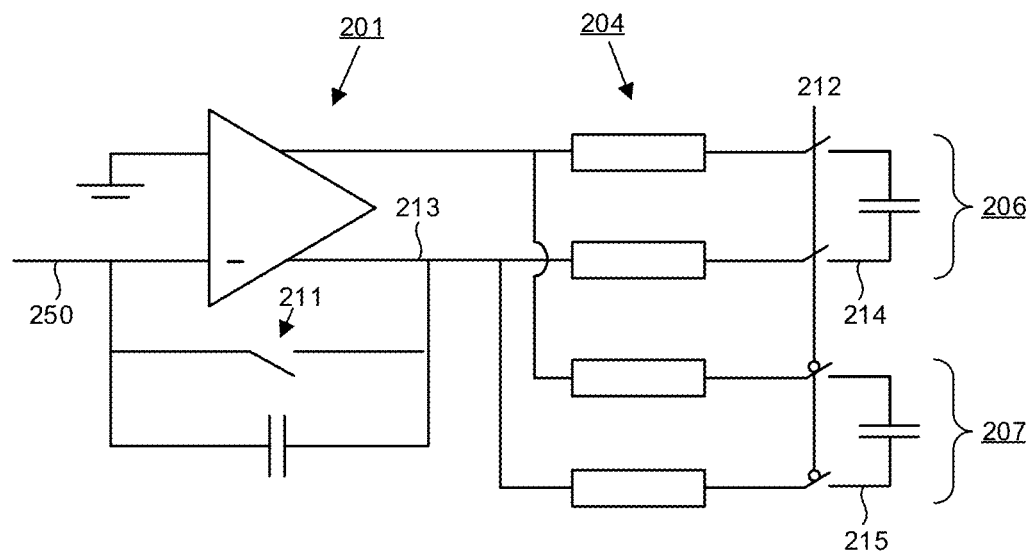
FIG. 6 depicts an example of an amplifier-free low pass filter.

Example operation of the amplifier-free low pass filter 204 is described with reference to FIGS. 6 and 7. As shown in FIG. 6, the amplifier-free low pass filter 204 comprises a first low pass filter module 206 and a second low pass filter module 207. The terms "first" and "second" are here used as labels to distinguish between the two low pass filter modules. The term "module" is used to refer to elements which provide the functionality required of each low pass filter module and could be used interchangeably with other equivalent terms such as "unit" or "device". The first low pass filter module 206 comprises a first RC filter and the second low pass filter module 207 comprises a second RC filter. A period of time in which a single, distinct measurement of the current is made (which may involve taking one sample or multiple samples of integrated current) is referred to herein as a sensing frame. By using the first and second low pass filter modules 206 and 207 alternately in different sensing frames, itis possible to obviate the need for an RC filter buffer 104 such as that used in the arrangement of FIG. 4.

Figure 7:
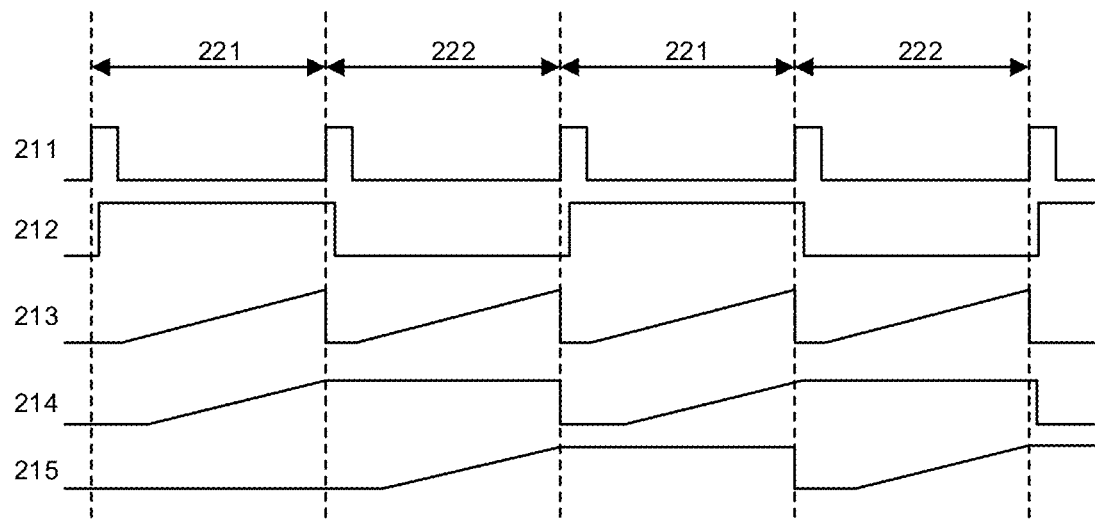
FIG. 7 depicts a timing diagram for operating the amplifier-free low pass filter of FIG. 5.

FIG. 7 depicts an example timing diagram illustrating example operation of the amplifier-free low pass filter 204 depicted in FIGS. 5 and 6. The horizontal axis in FIG. 7 represents time. The vertical axis shows variation with time of five signals 211-215 (described below). In the timing diagram of FIG. 7, four sensing frames are shown. The four sensing frames comprise two first sensing frames 221 and two second sensing frames 222. The first sensing frames 221 alternate with the second sensing frames 222.

A reset signal 211 is applied at the switch labelled 211. When the reset signal 211 is high, the first charge amplifier 201 is reset. The first charge amplifier 201 is thus reset at the start of each of the sensing frames 221, 222.

A flip signal 212 is applied on the line shown in FIG. 6. When the flip signal 212 is high, a capacitance component of the first low pass filter module 206 is connected to the output of the first charge amplifier 201. When the flip signal 212 is low, a capacitance component of the second low pass filter module 207 is connected to the output of the first charge amplifier 201. The capacitance component of the first low pass filter module 206 is thus connected to the output of the first charge amplifier 201 during each first sensing frame 221 and the capacitance component of the second low pass filter module 207 is connected to the output of the first charge amplifier 201 during each second sensing frame 222.

Signal 213 represents the output 213 of the first charge amplifier 201. During each sensing frame 221,222, the output 213 ramps up continuously as charge is integrated from the point immediately after the reset signal 211 has gone low to the point when the reset signal 211 next goes high at the end of the sensing frame 221,222. The processing circuit downstream from the first charge amplifier 201 obtains at least one sample of the output 213 from the first charge amplifier 201 in order to obtain a measure of the current input at point 250.

Signal 214 represents a signal level available for output from the first low pass filter module 206. The signal 214 ramps up in each first sensing frame 221 (when the first low pass filter module 206 is connected to the output 213 of the first charge amplifier 201) and remains flat in each second sensing frame 222 while the capacitance component of the first low pass filter module 206 holds the charge that was sampled during the preceding first sensing frame 221. The first low pass filter module 206 is thus in a storage mode during each second sensing frame 222. The charge sampled by the first low pass filter module 206 in each first sensing frame 221 can be read out at any time during the following second sensing frame 222.

Signal 215 represents a signal level available for output from the second low pass filter module 207. The signal 215 ramps up in each second sensing frame 222 (when the second lowpass filter module 207 is connected to the output 213 of the first charge amplifier 201) and remains flat in each first sensing frame 221 while the capacitance component of the second lowpass filter module 207 holds the charge that was sampled during the preceding second sensing frame 222. The second low pass filter module 207 is thus in a storage mode during each first sensing frame 221. The charge sampled by the second low pass filter module 207 in each second sensing frame 222 can be read out at any time during the following first sensing frame 221.

By using the circuit of FIG. 6 according to the timing diagram of FIG. 7, a first sample of the output 213 from the first charge amplifier 201 can be obtained in each sensing frame 221,222 without the need for an RC filter buffer (and associated amplifier) due to the sampling alternating between sampling via the first low pass filter module 206 and sampling via the second low pass filter module 207. The total number of amplifiers needed to implement the processing circuit is reduced and power consumption and/or heat dissipation is reduced.

The current measuring apparatus 200 of FIG. 5 reduces the need for amplifiers further by implementing second stage gain (corresponding to functionality provided within the CDS amplifier with second stage gain 105 of FIG. 4) using a capacitance component having a plurality of capacitors connected together electrically in parallel with respect to each other in place of each of the single capacitors of the first and second low pass filter modules 206 and 207 shown in FIG. 6.

Thus, an embodiment is provided in which, in each sensing frame in which sampling is not performed via the first low pass filter module 206 (e.g. a second sensing frame 222 in the example of FIG. 7), a sample from a directly preceding sensing frame (e.g. a first sensing frame 221 in the example of FIG. 7) is stored as charge on a capacitance component comprising a first plurality of capacitors 2061 in the first RC filter of the first low pass filter module 206.

Similarly, in each sensing frame in which sampling is not performed via the second lowpass filter module 207 (e.g. a first second sensing frame 221 in the example of FIG. 7), a sample from a directly preceding sensing frame (e.g. a second sensing frame 222 in the example of FIG. 7) is stored as charge on a capacitance component comprising a second plurality of capacitors 2071 in the second RC filter of the second low pass filter module 207.

In each second sensing frame 222, a selected attenuation (i.e. a negative gain) is applied to charge representing the information about the current to be measured by sampling charge only from a selected subset of the first plurality of capacitors 2061. Similarly, in each first sensing frame 221, a selected attenuation (i.e. a negative gain) is applied to charge representing the information about the current to be measured by reading out charge only from a selected subset of the second plurality of capacitors 2071.

In the example of FIG. 5, the first plurality of capacitors 2061 comprises four capacitors. In other embodiments, the first plurality of capacitors 2061 comprises a different number of capacitors. In an embodiment, in each first sensing frame 221 all of the capacitors in the first plurality of capacitors 2061 are connected into the circuit (all of the switches shown in the first low pass filter module 206 are closed), such that the first low pass filter module 206 operates optimally as an RC filter (i.e. to achieve maximum filtering). In each second sensing frame 222 selected switches in the first low pass filter module 206 are opened so as to connect only a subset of the capacitors of the first plurality of capacitors 2061 into the circuit. Only a proportion of the total charge stored on the first plurality of capacitors is thus made available for read out, thereby applying the desired attenuation. At a readout time in each second sensing frame, switches activated by the AND gate 2062 (when signal 212 is low and a readout signal, Srr, is high) allow the charge stored on the first plurality of capacitors 2061 to be read out.

The second plurality of capacitors 2071 are configured to operate in a similar manner. The second plurality of capacitors 2071 comprises four capacitors in the example but a different number could be provided if desired. In each second sensing frame 222 all of the capacitors in the second plurality of capacitors 2071 are connected into the circuit (all of the switches shown in the second low pass filter module 207 are closed), such that the second low pass filter module 20 207 operates optimally as an RC filter (i.e. to achieve maximum filtering). In each first sensing frame 221 selected switches in the second low pass filter module 207 are opened so as to connect only a subset of the capacitors of the second plurality of capacitors 2071 into the circuit. Only a proportion of the total charge stored on the second plurality of capacitors is thus made available for read out, thereby applying the desired attenuation. At a readout time in each 25 first sensing frame 221, switches activated by the AND gate 2072 (when 212 and Srr are both high) allow the charge stored on the capacitors to be read out.

An example timing diagram is shown in the bottom left of FIG. 5. Timing is shown for the case where multiple rows of pixels are present to allow readout from an array. Multiple readout signals Srr-r0, Srr-r1, Srr-rn are then provided for the $0^{th}$, $1^{st}$, $n^{th}$ row. The Srr signals are arranged to readout from each of the rows at a different time.

Figure 8:
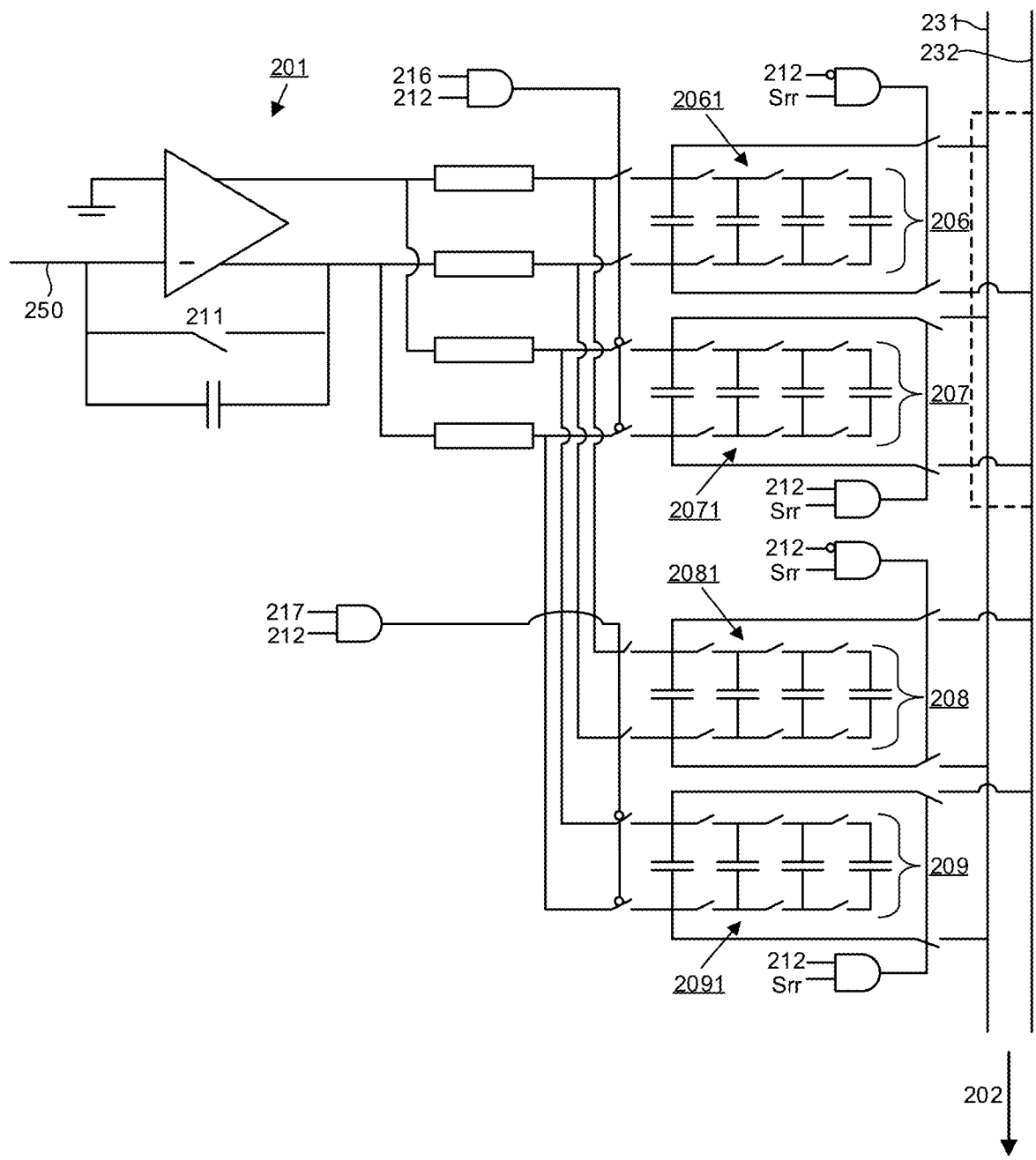
FIG. 8 depicts a portion of the current measuring apparatus of FIG. 5 adapted to perform correlated double sampling.
Figure 10:
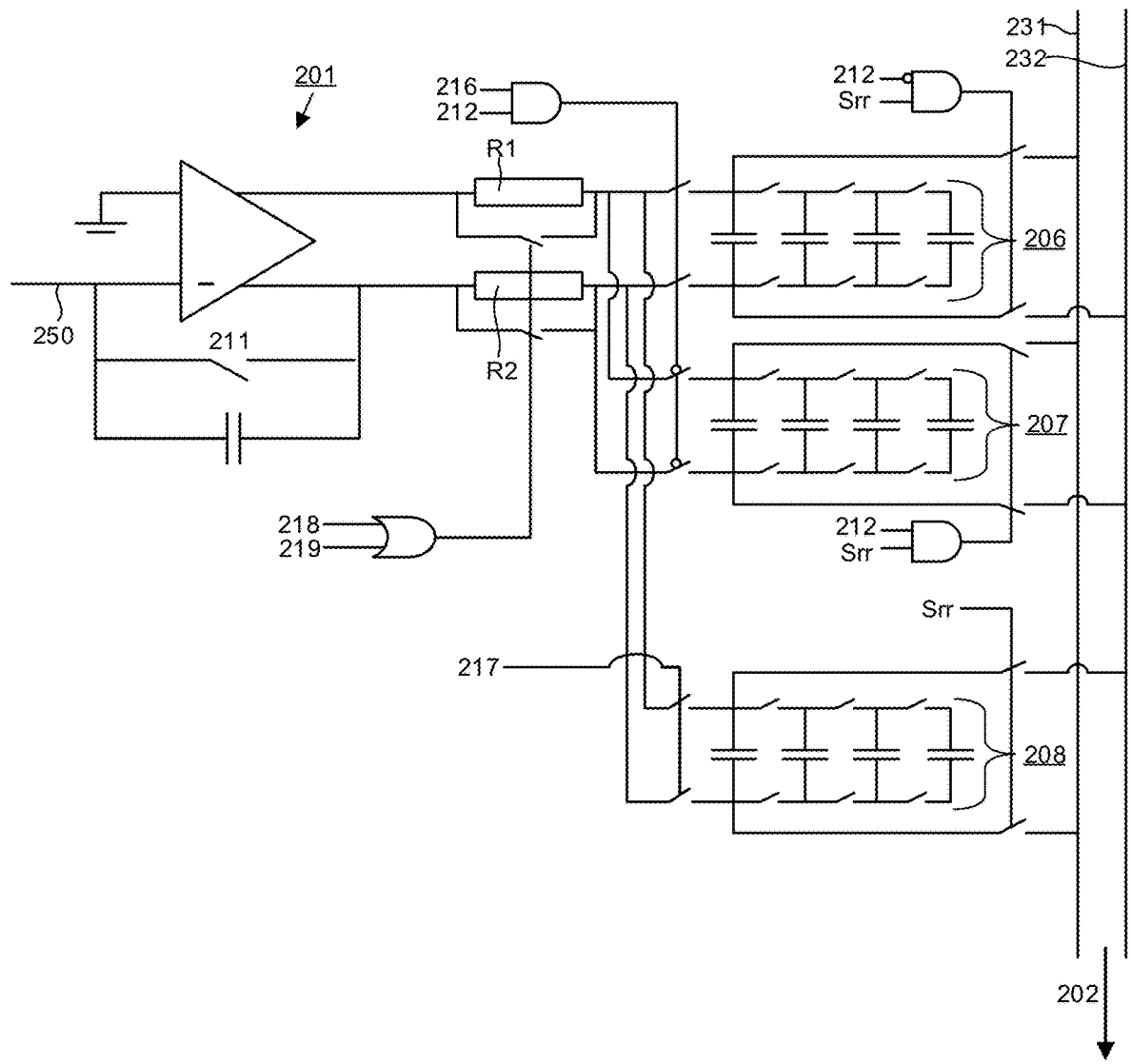
FIG. 10 depicts a variation of the current measuring apparatus of FIG. 8 requiring fewer distinct low pass filter modules.

FIGS. 8 and 10 depict alternative adaptations of the circuit of FIG. 5 to implement correlated double sampling. Both arrangements are examples of a class of embodiments in which a first sample and a second sample of the output 213 from the first charge amplifier 201 are obtained in each sensing frame 221, 222 and the processing circuit is configured to perform correlated double sampling using the first samples and second samples.

Figure 9:
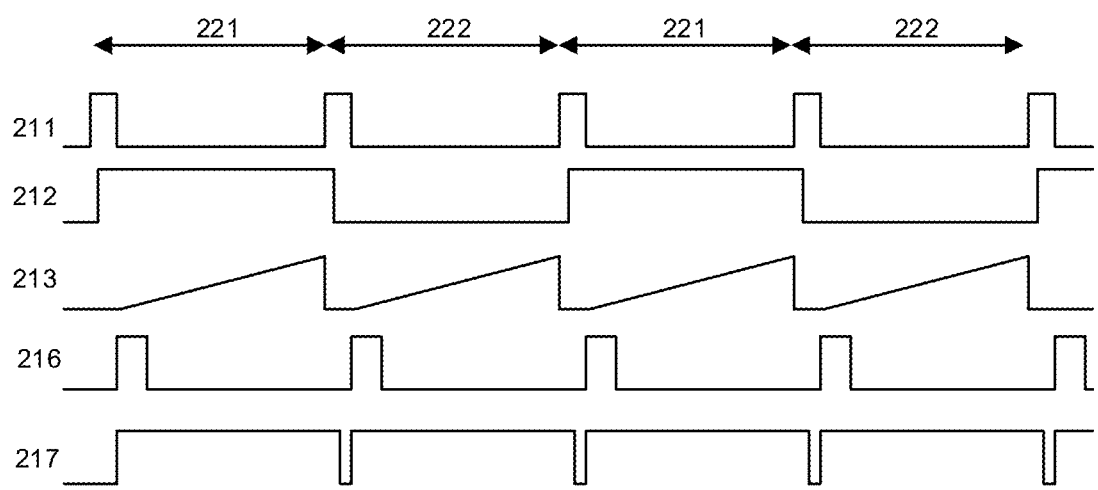
FIG. 9 depicts a timing diagram for operating the current measuring apparatus of FIG. 8.
Figure 11:
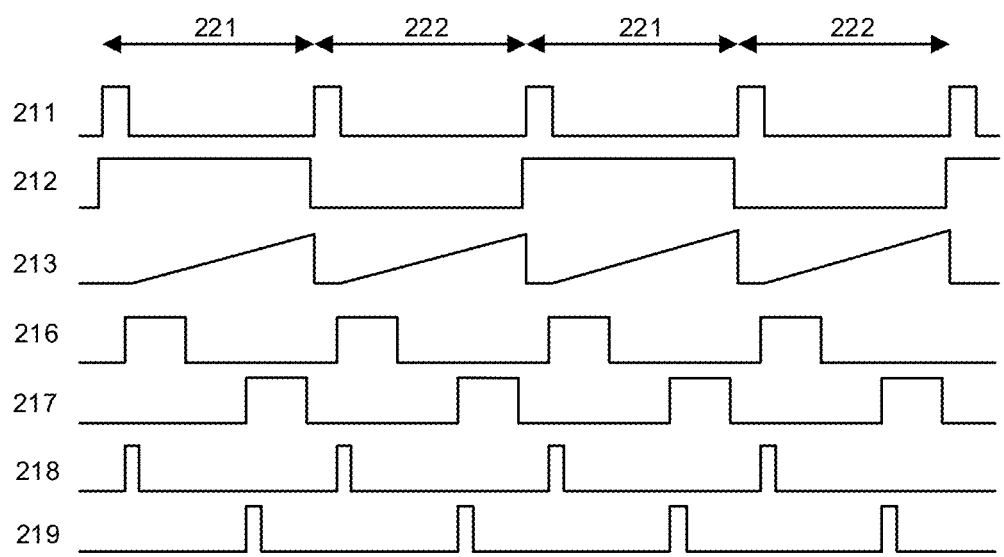
FIG. 11 depicts a timing diagram for operating the current measuring apparatus of FIG. 10.

An example timing diagram for the arrangement of FIG. 8 is shown in FIG. 9. An example timing diagram for the arrangement of FIG. 10 is shown in FIG. 11. Signals 211-213 correspond to the signals 211-213 described above with reference to FIG. 7. Additional signals 216 and 217 are provided to implement the correlated double sampling. Signal 216 determines, at the points where the signal falls from high to low, when the first sample of the correlated double sampling is obtained in each sensing frame 221, 222. Signal 217 indicates, at the points where the signal falls from high to low, when the second sample of the correlated double sampling is obtained in each sensing frame 221, 222.

To perform the correlated double sampling, the processing circuit comprises at least one further low pass filter module relative to the arrangement of FIG. 5. In a class of embodiments, of which FIGS. 8 and 10 are examples, the sampling of the first sample alternates from one sensing frame 221 to the next sensing frame 222 between sampling via a first low pass filter module 206 and sampling via a second low pass filter module 207. In the example of FIGS. 8 and 9, the first sample is sampled via the first low pass filter module 206 in each first sensing frame 221 and read out from the first low pass filter module 206 (when in storage mode) in the following second sensing frame 222. The first sample is sampled via the second low pass filter module 207 in each second sensing frame 222 and read out from the second low pass filter module 207 (when in storage mode) in the following first sensing frame 221. FIGS. 8 and 10 respectively depict two possibilities for sampling the second sample in this scenario. In both cases, the sampling of the second sample is performed via the at least one further low pass filter module.

In the arrangement of FIG. 8, the at least one further low pass filter module comprises a third low pass filter module 208 and a fourth low pass filter module 209. In this arrangement, sampling of the second sample alternates from one sensing frame 221 to the next sensing frame 222 between sampling via the third low pass filter module 208 and sampling via the fourth low pass filter module 209. In the example of FIGS. 8 and 9, the second sample is sampled via the third low pass filter module 208 in each first sensing frame 221 and read out from the third low pass filter module 208 (when in storage mode) in the following second sensing frame 222. The second sample is sampled via the fourth low pass filter module 209 in each second sensing frame 222 and read out from the fourth low pass filter module 209 (when in storage mode) in the following first sensing frame 221. In the example shown, the third low pass filter module 208 comprises a third RC filter and the fourth low pass filter module 209 comprises a fourth RC filter. Each of the third RC filter and the fourth RC filter may be configured in any of the ways described above for the first RC filter and the second RC filter respectively. In the embodiment shown, a capacitance component of the third RC filter comprises a third plurality of capacitors 2081. In an embodiment, a capacitance component of the fourth RC filter comprises a fourth plurality of capacitors 2091. In the example shown, each plurality of capacitors 2081 and 2091 comprises four capacitors. In other embodiments, each of either or both of the third and fourth pluralities of capacitors 2081 and 2091 may comprise a different number of capacitors. The third and fourth pluralities of capacitors 2081 and 2091 may operate in the same manner as the first and second pluralities of capacitors 2061 and 2071. Namely, when the respective third or fourth RC filter is operating as a filter all of the capacitors may be connected to the circuit to optimize filtering. When the respective third or fourth RC filter is being read from, only a subset of the capacitors may be connected into the circuit in order that only a proportion of the total charge stored on the plurality of capacitors is made available for read out, thereby applying the desired attenuation.

In an embodiment, a difference between the first sample and second sample in each sensing frame 221, 222 is implemented by combining with reversed polarities, as exemplified in the broken line square in FIG. 8, an output from the low pass filter module that stores charge corresponding to the first sample (e.g. the first plurality of capacitors 2061 or the second plurality of capacitors 2071 in FIG. 8) and an output from the low pass filter module that stores charge corresponding to the second sample (e.g. the third plurality of capacitors 2081 or the fourth plurality of capacitors 2091 in FIG. 8). Thus, the first low pass filter module 206 and the second low pass filter module 207 are connected to the output lines 231 and 232 leading towards the second charge amplifier 202 in a reverse configuration relative to the connections to the output lines 231 and 232 from the third low pass filter module 208 and the fourth low pass filter module 209.

FIG. 10 depicts an example of an embodiment in which the sampling of the second sample is performed via the same single one of the at least one further low pass filter module for all sensing frames. In the example shown there is only one further low pass filter module 208. The sampling of the second sample is performed exclusively via the single further low pass filter module for all sensing frames. The obtaining of the second sample without requiring two further low pass filter modules (as in the embodiment of FIGS. 8 and 9) is achieved by arranging for each of the first low pass filter module 206, second low pass filter module 207 and further low pass filter module 208 to be reset in each sensing frame 221, 222 in which the low pass filter module in question obtains a sample (e.g. the first low pass filter module 206 is reset at least in sensing frames 221 in which the first low pass filter module 206 obtains the first sample, the second low pass filter module 207 is reset at least in sensing frames 222 in which the second low pass filter module 207 obtains the first sample, and the further low pass filter module 208 is reset in every sensing frame 221 and 222 to obtain the second sample. The resetting of each low pass filter module is performed by bypassing a resistance component of an RC filter of the low pass filter module. Furthermore, low noise is achieved by arranging for the timing of the resetting of each low pass filter module to be such that each of the first sample and the second sample is obtained an equal time after the resetting of the low pass filter module via which the sample is sampled.

An example timing diagram is shown in FIG. 11. Signals 211-213 correspond to the signals 211-213 described above with reference to FIG. 7. Additional signals 216 and 217 are provided to implement the correlated double sampling. Further additional signals 218 and 15 219 are provided to reset the low pass filter modules 206, 207 and 208 by opening switches in parallel to the resistors labelled R1 and R2 in FIG. 10. Each low pass filter module 206, 207 and 208 in this example is thus reset by bypassing the resistance component of the RC filter in each low pass filter module. The signals 211-213 and 216-219 cause the first sample to be obtained in each first sensing frame 221 via the first low pass filter module 206 and to be obtained in each second sensing frame 222 by the second low pass filter module 207. The second sample is obtained in every sensing frame (i.e. every first sensing frame 221 and every second sensing frame 222) by the further low pass filter module 208. This functionality is enabled by each of the first sample and the second sample being obtained an equal time after are setting of the low pass filter module via which the sample is sampled, which is implemented in the example shown by having a pulse in signal 218 or signal 219 coinciding with the start of each of the pulses in the signals 216 and 217 and being shorter in length than each of the pulses in the signals 216 and 217. Thus, at the start of each pulse in signal 216, which controls when the first samples are obtained, the signal 218 causes all of the low pass filter modules to be reset (i.e. with the resistance component bypassed so that the capacitance component is connected directly to the first charge amplifier 201). The resetting of each low pass filter module causes the plurality of capacitors to charge quickly to a voltage defined by the charge at the output of the first charge amplifier 201 at the corresponding point in time. After each reset of a low pass filter module, the low pass filter module is allowed to settle before a first sample or a second sample is taken.

The two signals 216 and 217 implementing the correlated double sampling overlap the two signal 218 and 219 implementing the resetting. Signals 216 and 218 operate together and signals 217 and 219 operate together. The first and second samples are obtained on the falling edges of the pulses in the signals 216 and 217. To achieve the ideal noise performance the time difference between the falling edges of the pulses in 218 and 216 should be the same as the time difference between the falling edges of the pulses in 219 and 217 (an example satisfying the above-mentioned optional requirement that the first sample and the second sample are obtained an equal time after a resetting of the low pass filter module via which the sample is sampled).

Noise in circuits of the type described above with reference to FIGS. 10 and 11 has two components: a switched component and a continuous component. When the reset of the first charge amplifier 201 is released (i.e. goes low) the wideband noise of the first charge amplifier 201 is folded into the baseband defined by the sampling frequency. This results in a random offset of the first charge amplifier 201 that changes every field. This is the switched component of the noise. The continuous component of the noise, which comes for example from the first charge amplifier, contributes in addition to the switched component of the noise.

The correlated double sampling is intended to reduce the switched component of the noise, which is a low frequency component. RC filtering implemented via the low pass filter modules reduces the continuous component of the noise. However, the output from each low pass filter module takes time to settle onto the ramping output of the first charge amplifier 201. When performing correlated double sampling, a long delay may therefore be introduced before the first sample is obtained. This is undesirable, however, because it results in the measured signal being reduced, which effectively increases noise. An alternative approach is to obtain the first sample before the low pass filter module has settled, but this may result in a residual switched component of noise.

Figure 12:
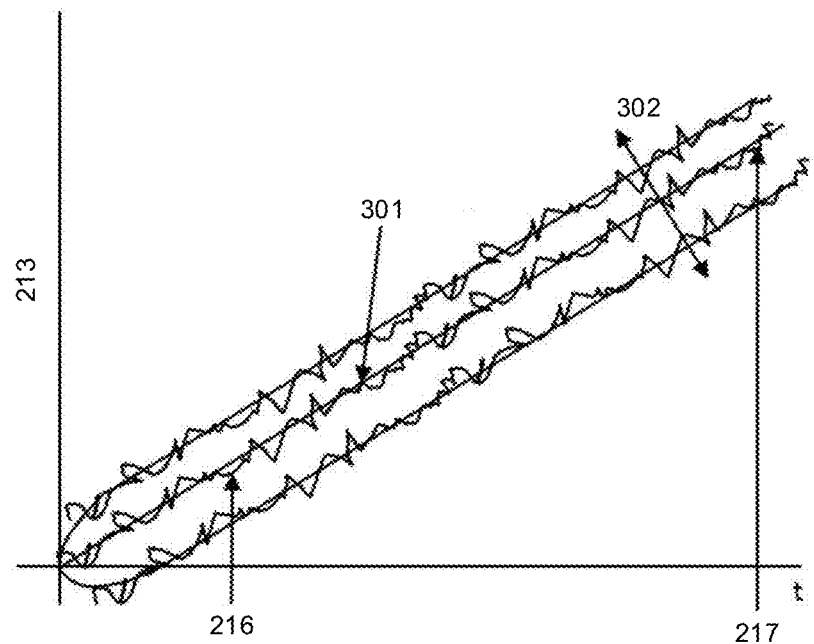
FIGS. 12-15 are schematic graphs depicting the origin of residual correlated double sampling noise and how it can be avoided by taking the first and second samples an equal time after a reset operation.
Figure 13:
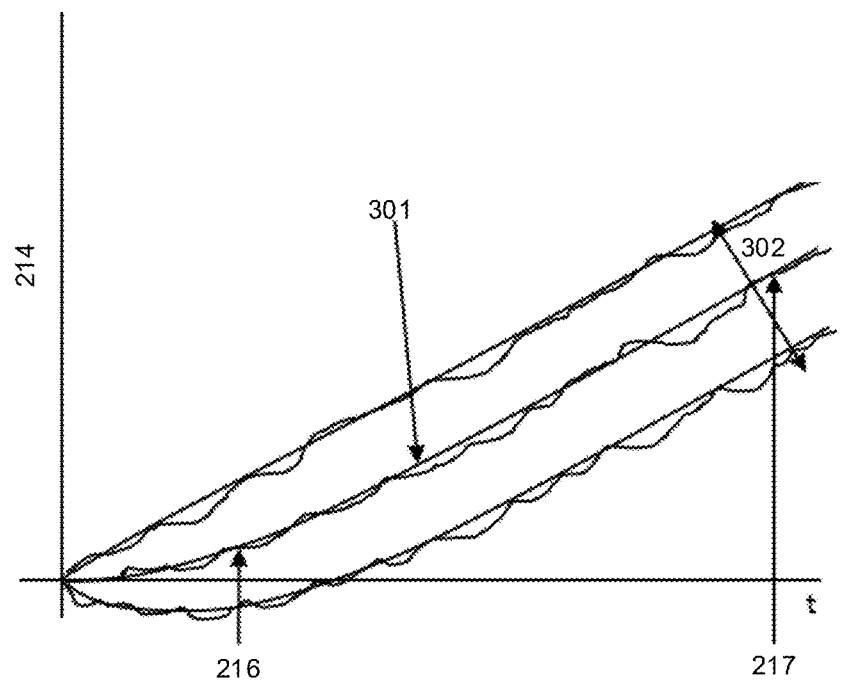
Figure 14:
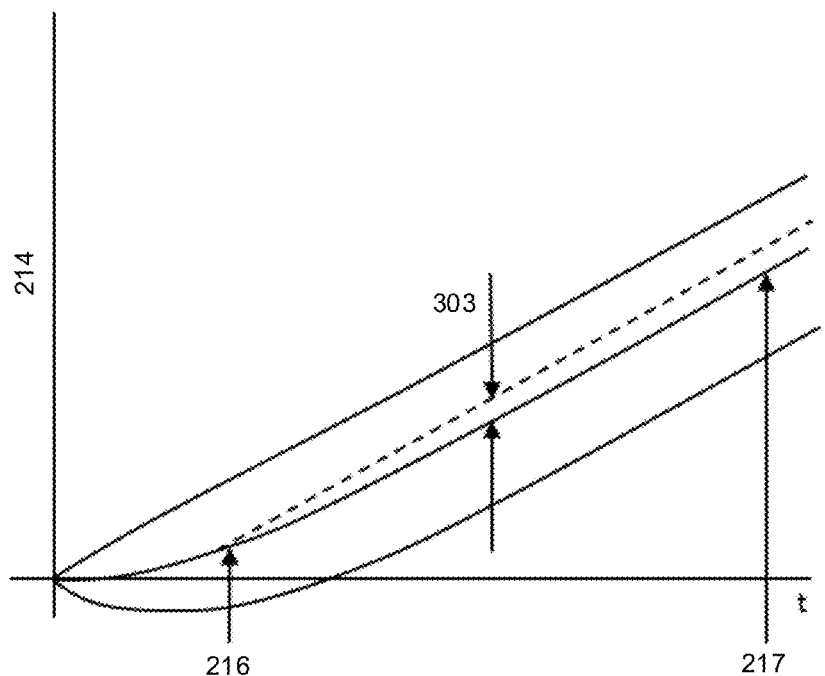

These effects are illustrated in FIGS. 12-15. The horizontal axis in each of FIGS. 12-15 represents time. The vertical axis in FIG. 12 represents an output 213 from the first charge amplifier 201 (showing a ramp corresponding to integration of a current to be measured) for three example realisations (each representing a different realisation of the random noise made up of the continuous component 301 and the switched component 302 mentioned above). The switched component of noise causes the ramp (depicted by the three smooth background curves) to be shifted vertically (after the first charge amplifier 201 comes out of reset and starts to integrate charge). The continuous component of noise is shown as a rapidly fluctuating signal superimposed on top of each smooth background curve). Applying a low pass filter to the output (e.g. one or more of the low pass filter modules described above) leads to a filtered output 214, as shown schematically in FIG. 13. The filtering smooths the continuous component 301 of the noise, but has no effect on the switched component 302 of the noise. Correlated double sampling points 216 and 217 are shown on the figure (point 216 indicates a time when a first sample is sampled and point 217 indicates a time when a second sample is sampled). The correlated double sampling should entirely remove the switched component 302 of the noise. However, as indicated in FIG. 14 (which shows the filtered output 214 with only the switched component 302 of the noise present (the continuous component 301 of the noise has been artificially set to zero for clarity), the first sample is sampled before the filter has settled to the continuous (straight line part) of the ramp. This leads to a residual correlated double sampling noise 303, as indicated by the broken line curve in FIG. 14.

The approach described above with reference to FIGS. 10 and 11 reduces or removes any negative impact from this effect by arranging for the first sample and the second sample of the correlated double sampling to be obtained an equal time after a resetting of the low pass filter module via which the sample is sampled. The result of this is that the first sample is obtained at exactly the same point during the settling of the low pass filter module as the second sample.

Figure 15:
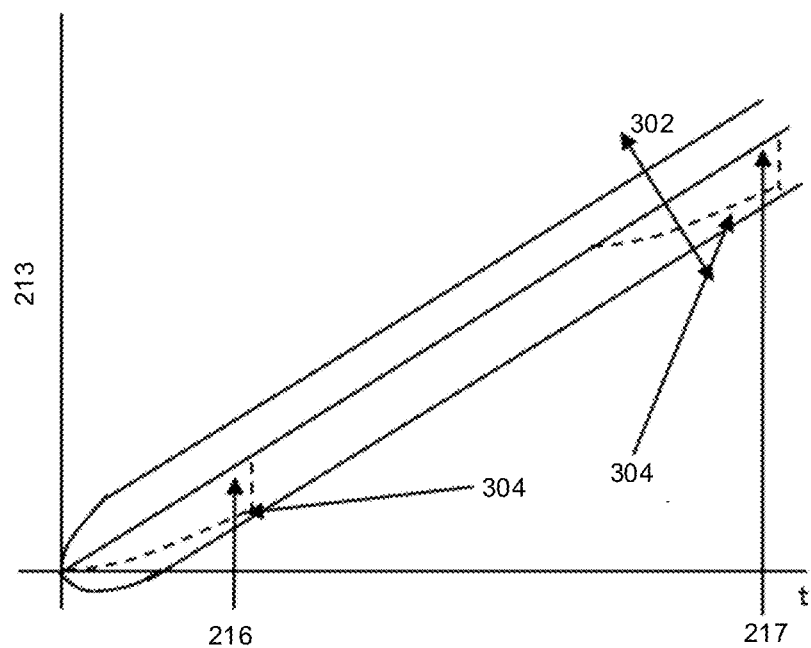

FIG. 15 shows the method. The broken line curves 304 schematically depict settling of a low pass filter module just before each of the first sample and the second sample are sampled (at points 216 and 217 respectively). The method does not wait for the low pass filter module to settle, but rather obtains the first sample and the second sample at the same time after the settling begins. The correlated double sampling involves taking the difference between the two samples (the first sample and the second sample) and the residual switched component of noise is therefore eliminated (it makes the same contribution to the first sample and the second sample). In FIG. 11, the timing diagram shows pulses in the 216 and 217 signals. The output of the low pass filter module starts to settle within the respective pulses in the 216 and 217 signals and the first and second samples are sampled as the respective pulses in the 216 and 217 signals go low. The broken line curves 304 in FIG. 15 thus correspond to the output of the low pass filter module when the pulses in the 216 and 217 signals are high.

Although more complex in terms of timing signals, the approach of FIGS. 10 and 11 can be implemented using fewer capacitors and fewer resistors in the low pass filter modules than the approach of FIGS. 8 and 9, thereby saving silicon area.

Figure 16:
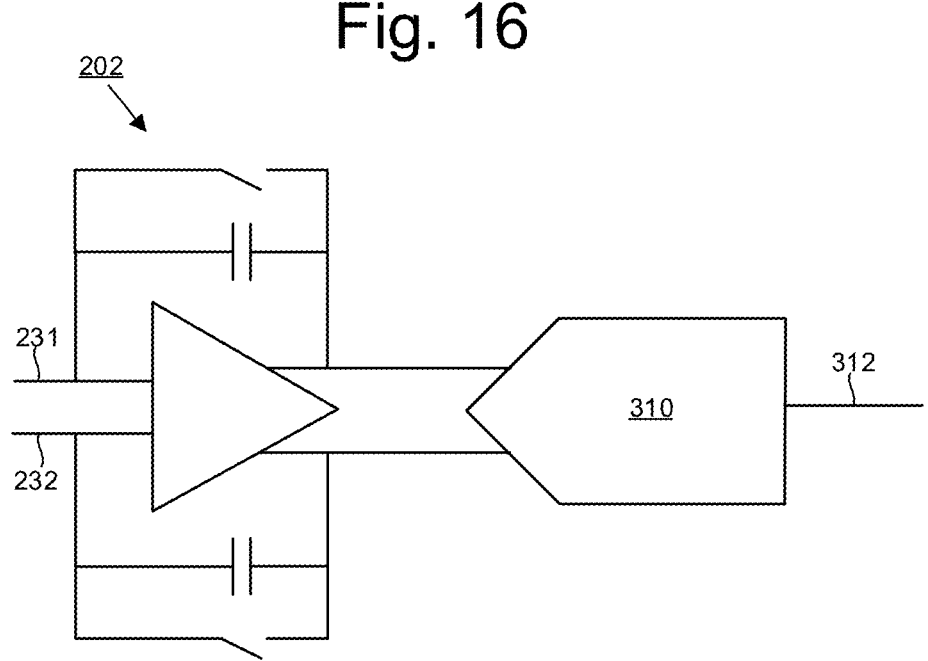
FIG. 16 depicts an arrangement in which an SAR ADC is provided after the second charge amplifier to provide a digital output signal.

FIG. 16 depicts an embodiment in which an SAR ADC 310 is provided after the second charge amplifier 202 to provide a digital output signal 312. This arrangement is compatible with any of the embodiments discussed above with reference to FIGS. 5-15. The use of the SAR ADC reduces power requirements relative to other ADCs, although other ADCs could still be used as an alternative. Provision of the SAR ADC after the second charge amplifier 202 provides improved efficiency in terms of amplifiers (i.e. can be implemented uses fewer amplifiers) if used after the second charge amplifier 202.

The SAR ADC is one of the most power efficient ADC architectures but there are some issues that need to be considered. The linearity of the SAR ADC is usually limited to 10 bits. Higher linearity can be achieved using techniques such as sigma delta modulation, but this may increase power consumption. Another issue is that the SAR ADC can be relatively large, so it may be desirable to multiplex several columns to each SAR ADC provided. This approach would require the large input load of the SAR ADC to be driven rapidly, which could increase power consumption.

Figure 17:
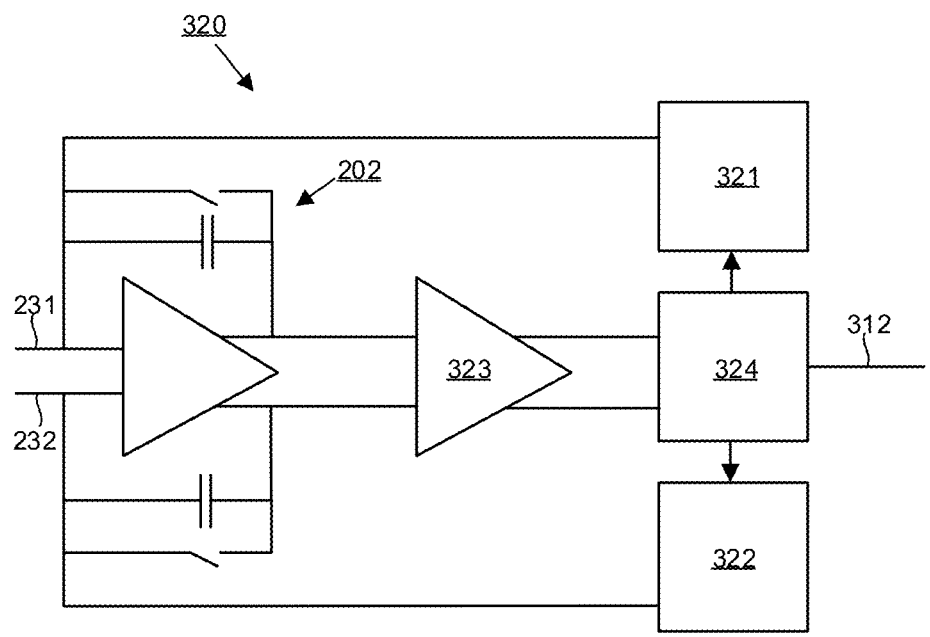
FIG. 17 depicts an example multi-slope ADC based alternative to the arrangement of FIG. 16.

Another ADC architecture is the multi-slope ADC. Using this architecture with the second charge amplifier 202 allows charge readout from the pixels and analog to digital conversion to be performed within the same module. This is efficient in terms of circuit area and power. FIG. 17 shows an example arrangement of a multi-slope ADC architecture 320 incorporating the second charge amplifier 202. The multi-slope ADC architecture 320 can be used in combination with any of the embodiments discussed above with reference to FIGS. 5-15.

The multi-slope ADC architecture 320 comprises the second charge amplifier 202, a first charge DAC feedback unit 321, a second charge DAC feedback unit 322, a comparator 323, and a digital control unit 324 configured to output the digital output signal 312. In operation, charge received from the upstream circuitry leading from the first charge amplifier 201 (as described above with reference to FIGS. 5-15) is presented by the second charge amplifier 202 as a voltage to the comparator 323 of the multi-slope ADC architecture 320. After settling to an accurate voltage, the analog to digital conversion can proceed. This can be done by either current or charge feedback. FIG. 17 depicts an example in which charge is feedback. Packets of current or charge (as in FIG. 17) are fed back (by the first and second charge DAC feedback units 321 and 322 in the example shown) so that the outputs of the second charge amplifier 202 are drawn to a crossing point of the comparator 323. The number of current or charge steps required to do this represents the most significant bit (MSB) value. The converter then changes to a second slope where least significant bits (LSBs) are found via the same approach to achieve a full digital data conversion. Further slopes can be added if desired. The arrangement provides a dual function of charge readout from the pixel and ADC conversion, which saves power and silicon area. The multi-slope ADC architecture 320 could be adapted to operate in a single slope mode, but this would reduce the conversion rate and may be less practical for some applications.

Figure 18:
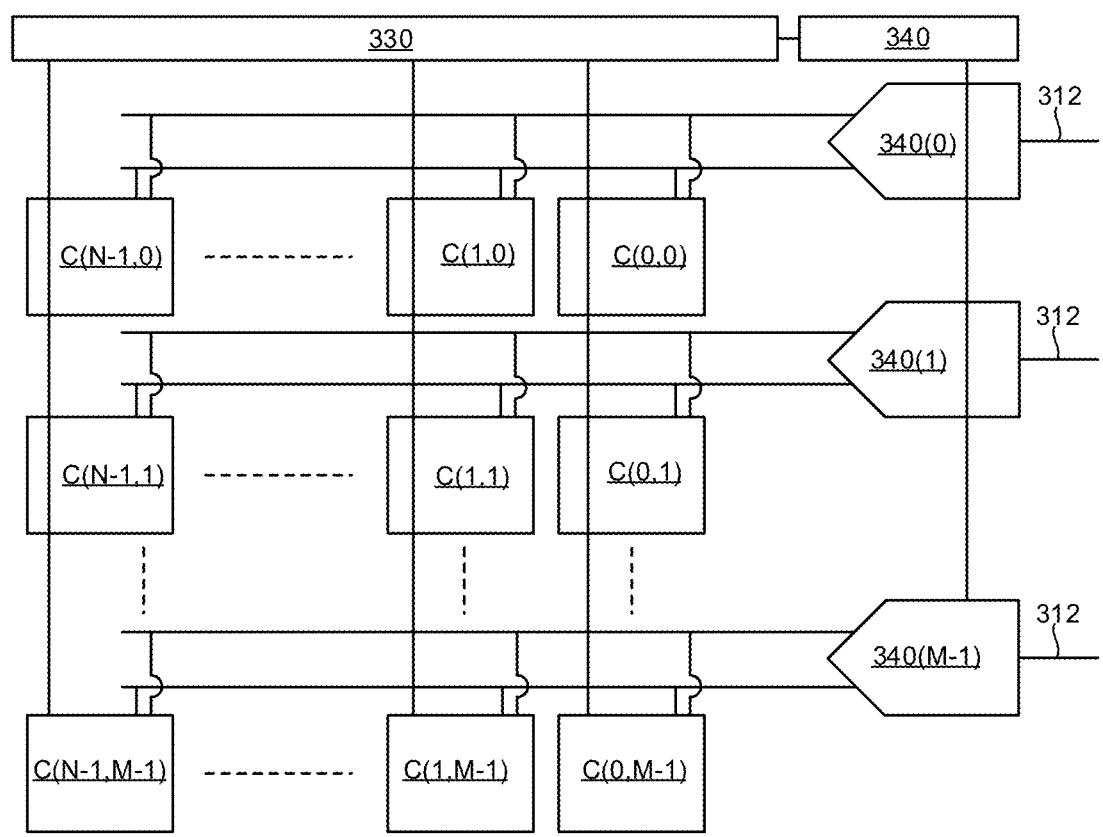
FIG. 18 depicts an example architecture for enabling readout from a plurality of channels in a matrix array.

FIG. 18 shows schematically an architecture for enabling readout from a plurality of channels (which may be referred to as pixels) in a matrix array. Each channel is labelled as C(i,j), where i indicates row number and j indicates column number. Each channel comprises circuitry for measuring a current that may be configured according to any of the embodiments described above with reference to FIGS. 5-15. In the example shown, N channels are provided per column (arranged horizontally). The N channels may be read according to a timing diagram such as that depicted in the lower part of FIG. 5 (via signals Srr-r0, Srr-r1, etc.). The N channels in each column connect to an integrated component 340(j) configured to perform the dual functionality of charge readout (via the second charge amplifier 202) and analog to digital conversion, as described above with reference to FIGS. 15 and 16. Any of the embodiments discussed above in connection with FIGS. 15 and 16 may be used to implement the integrated component 340(j). In the example shown, M columns are provided, so there are M integrated components 340(j), which each output digital data streams 312 that can be read from an ASIC using many standard techniques. The channels are addressed by a row controller 330 which produces the Srr signals shown in FIG. 5. The Srr signal is activated once per sensing frame 221,222 per channel C (i,j). In the embodiment shown, each integrated component 340(j) addresses a single column. In other embodiments, one or more of the integrated components 340(j) may be configured to address multiple columns.

The following description introduces an alternative reset mechanism for resetting a charge amplifier, which is referred to herein as a charge balancing soft reset. After this introduction, embodiments making use of the charge balancing soft reset will be described.

Figure 19:
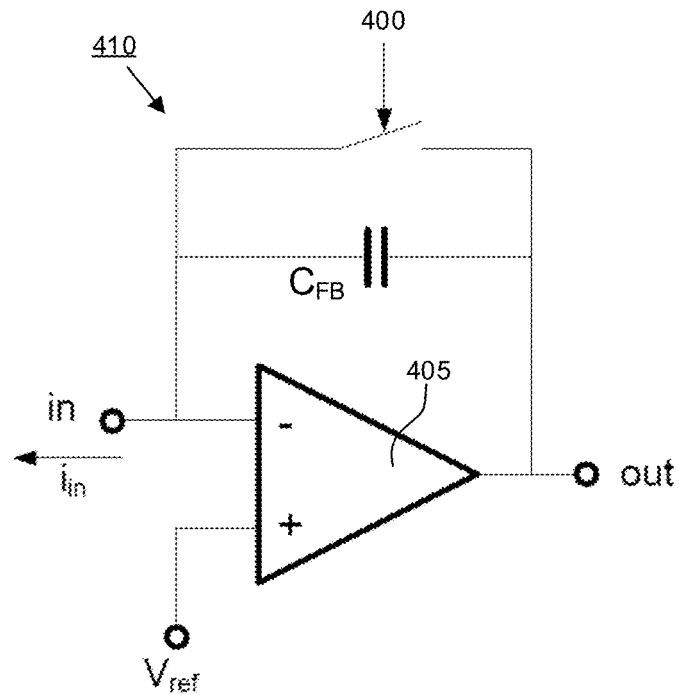
FIG. 19 depicts a charge amplifier in a configuration suitable for detection of small currents from a sensor.

FIG. 19 depicts a charge amplifier 410 in a configuration suitable for detection of small currents from a sensor element. The sensor element behaves as current source and the charge amplifier performs a charge to voltage conversion by integrating the charge.

Figure 20:
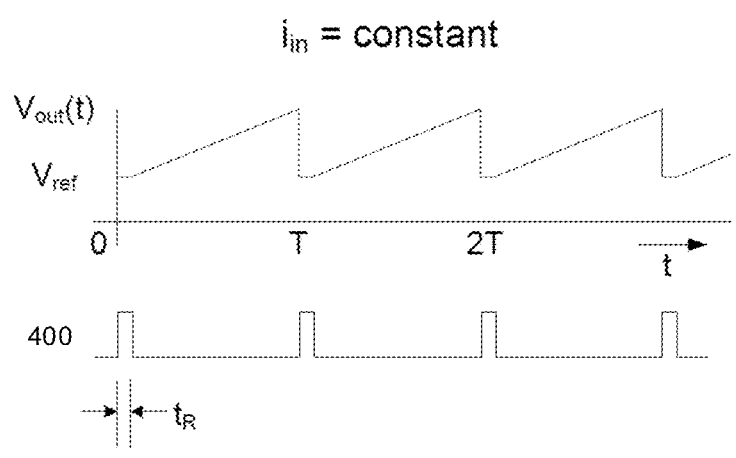
FIG. 20 depicts a timing diagram for operating the circuit of FIG. 19.

When the reset switch 400 is opened, the input current $i_{in}$ is integrated in capacitor $C_{FB}$. The gain of the circuit depends on the feedback network. In some applications a resistor is used in parallel to the feedback capacitor, but this is unpractical when currents in the pA range must be detected and thus very high gains are required. In such cases, the amplifier is reset after every integration interval as shown in FIG. 20.

Figure 21:
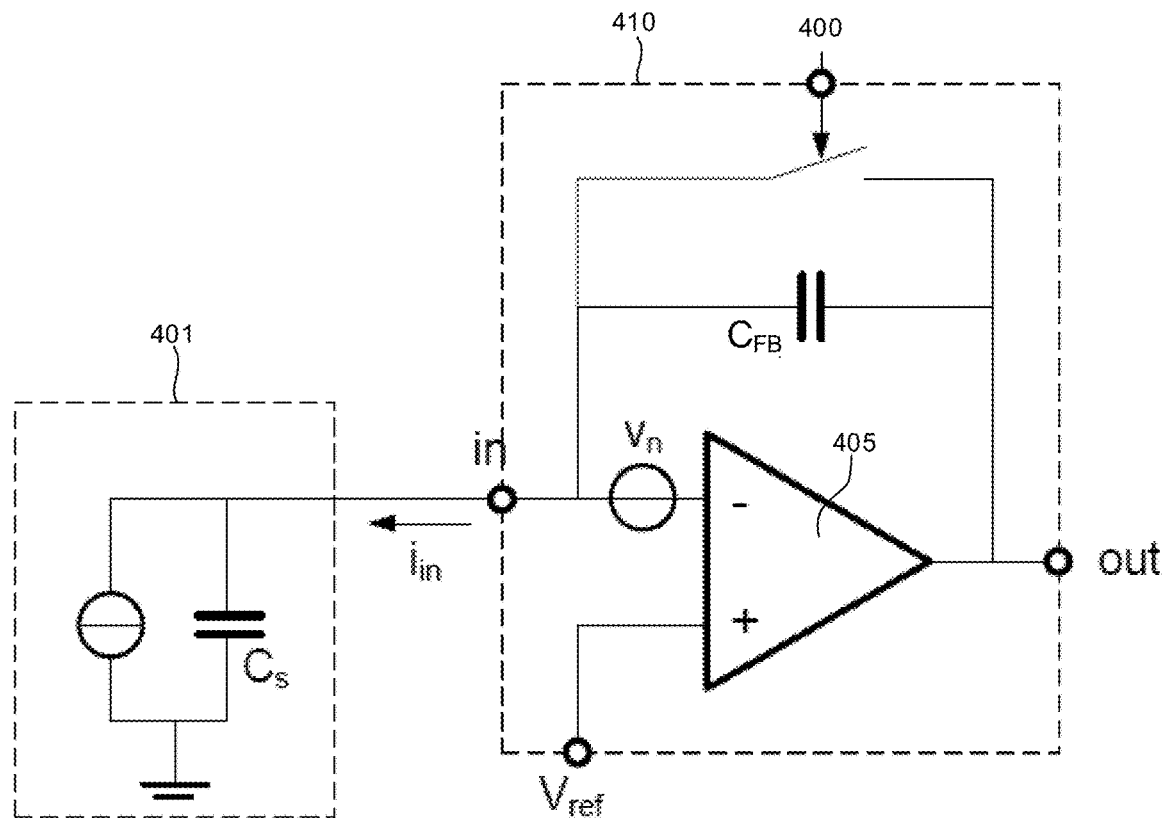
FIG. 21 depicts a combination of a charge amplifier of the type depicted in FIG. 19 with a sensor.

During reset the integration of the input current is interrupted. The reset operation results in noise folding, increasing the output noise level. The noise from an operational amplifier (OpAmp) 405 can be represented by the input noise voltage source $v_n$; see FIG. 21. FIG. 21 depicts a combination of a charge amplifier 410 of the type depicted in FIG. 19 with a sensor 401 (behaving as a source of a current to be measured by the charge amplifier 410). The combination of charge amplifier 410 with the sensor 401 provides a voltage gain of $C_s/C_{FB}$ for the OpAmp 405 noise voltage $v_n$. At the moment the reset switch 400 is opened, the amplified OpAmp 405 noise is sampled on the integration capacitor $C_{FB}$. In the time domain, this is seen as a randomly varying offset voltage at the start of every integration period and is equivalent to the noise folding effect usually analysed in the frequency domain. To limit the overall noise, the output signal of the charge amplifier 410 is usually filtered using low pass and/or high pass filters. Filters can be passive or discrete-time. For example, a correlated double-sampling (CDS) filter can be applied as a high-pass filter. A high-pass filter is an effective means to filter low-frequency noise that can be high for practical OpAmps 405. Most CMOS amplifiers are dominated by 1/f-noise at low frequencies.

The alternative charge balancing soft reset approach is now described. The charge balancing soft reset approach replaces the charge amplifier reset operation described above with reference to FIGS. 19-21 with a mechanism based on charge cancellation. The charge balancing soft reset approach promotes reduction of low frequency noise such as that which might be produced by noise folding. The charge balancing soft reset approach is also compatible with output filtering being applied to further reduce noise.

A further advantage of the charge balancing soft reset approach is that integration of the input signal occurs without interruption. In the hard reset approach of the arrangement of FIGS. 19-21 the charge amplifier 410 does not respond to input currents when the charge amplifier 410 is held in reset. The charge balancing soft reset approach allows uninterrupted integration, which makes it possible to respond to events that occur during the reset period that would otherwise not be seen.

The charge balancing soft reset approach can be implemented in such a way that a charge amplifier 204 is still effectively reset once in a sensing frame T.

Figure 22:
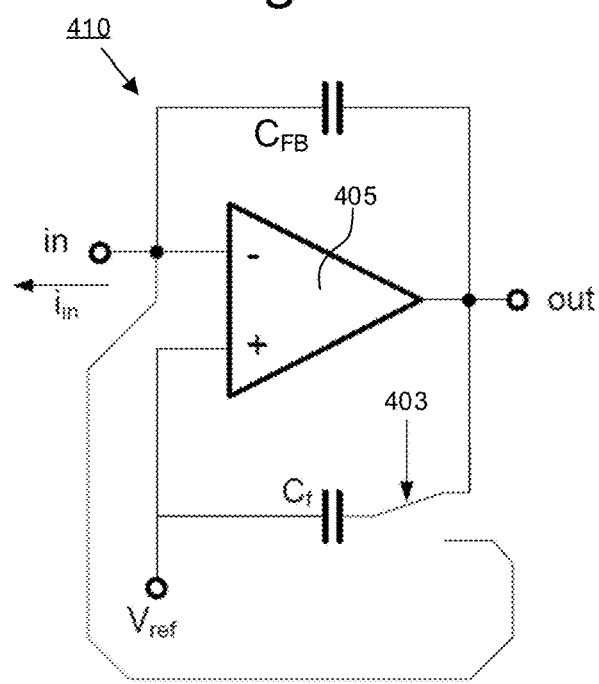
FIG. 22 depicts an example arrangement of implementing a charge balancing soft reset.

FIG. 22 depicts an arrangement for implementing the charge balancing soft reset approach. If it is assumed that an ideal OpAmp 405 is used inside the charge amplifier 410 of FIG. 22 (e.g. with no input offset, no noise and infinite open-loop gain) then the voltage across the feedback capacitor $C_{FB}$ at the end of an integration period equals $v_{out}(T) - V_{ref}$. In the arrangement shown, a second capacitor $C_f$ is connected between the output and the reference voltage $V_{ref}$ as long as control signal 403 is low.

As long as control signal 403 is low, the voltage across $C_f$ is equal to the voltage across $C_{FB}$, and if it is chosen that $C_f = C_{FB}$ the charge at $C_f$ will be equal to the charge at $C_{FB}$. When control signal 403 becomes high, capacitor $C_f$ is disconnected from the output and connected to the amplifier signal input, e.g. virtual ground. This results in a discharge of capacitor $C_f$ into $C_{FB}$ that effectively resets capacitor $C_{FB}$ in a soft manner. During this process of charge balancing the integration of the input signal continues.

To obtain exact cancellation of the charge at the end of the integration period, we need to choose $C_f = C_{FB}$. If the charge amplifier 410 has programmable gain via a programmable capacitor $C_{FB}$, then capacitor $C_f$ must also be programmable.

Additional control signals are not necessary to implement the charge balancing soft reset. The reset signal 400 that controls the reset switch in the implementation of FIG. 19 can be used to control charge balancing switches such as the switch in FIG. 22 receiving the balancing signal 403 in the circuit of FIG. 22. There is, therefore, no increase in power dissipation.

Figure 23:
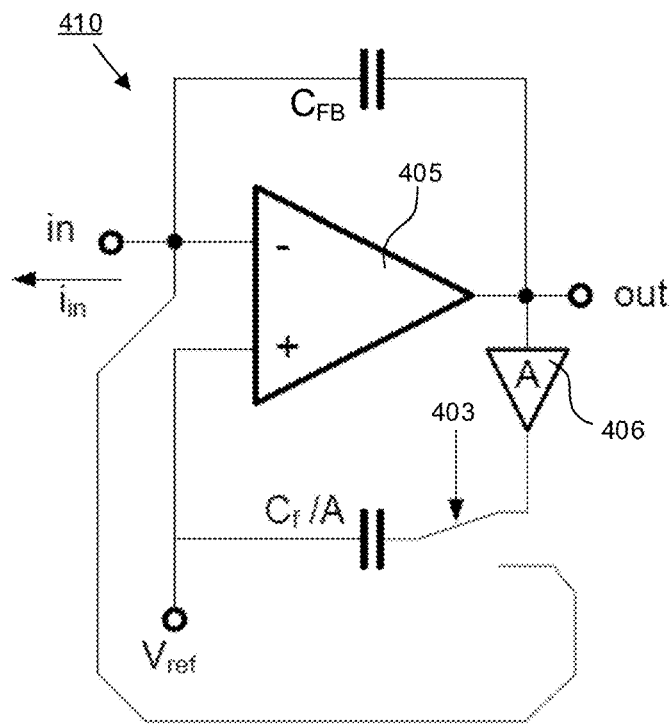
FIG. 23 depicts a variation on the arrangement of FIG. 22 in which a loading of the operational amplifier is reduced using a buffer amplifier.

The circuit of FIG. 22 adds capacitive loading to the output of the OpAmp 405. Depending on the properties of the OpAmp 405 and capacitor values, stability of the circuit may be reduced. An alternative implementation is shown in FIG. 23 that reduces the loading of the OpAmp 405 by the introduction of a buffer amplifier 406. If the buffer amplifier 406 has a gain A, capacitor $C_f$ needs to be scaled to $C_f = C_{FB}/A$ to achieve the correct amount of charge during feedback. The introduction of buffer amplifier 406 can also be exploited to save chip area in the case of a large capacitor area for $C_{FB}$.

The value of the duplicate capacitor will not be an exact copy of the integration capacitor due to mismatch. This leads to a systematic offset of the output voltage. Other imperfections such as charge injection from the switching network also lead to a systematic output offset. If desired, such an offset can be removed by high-pass filtering of the output signal.

Figure 24:
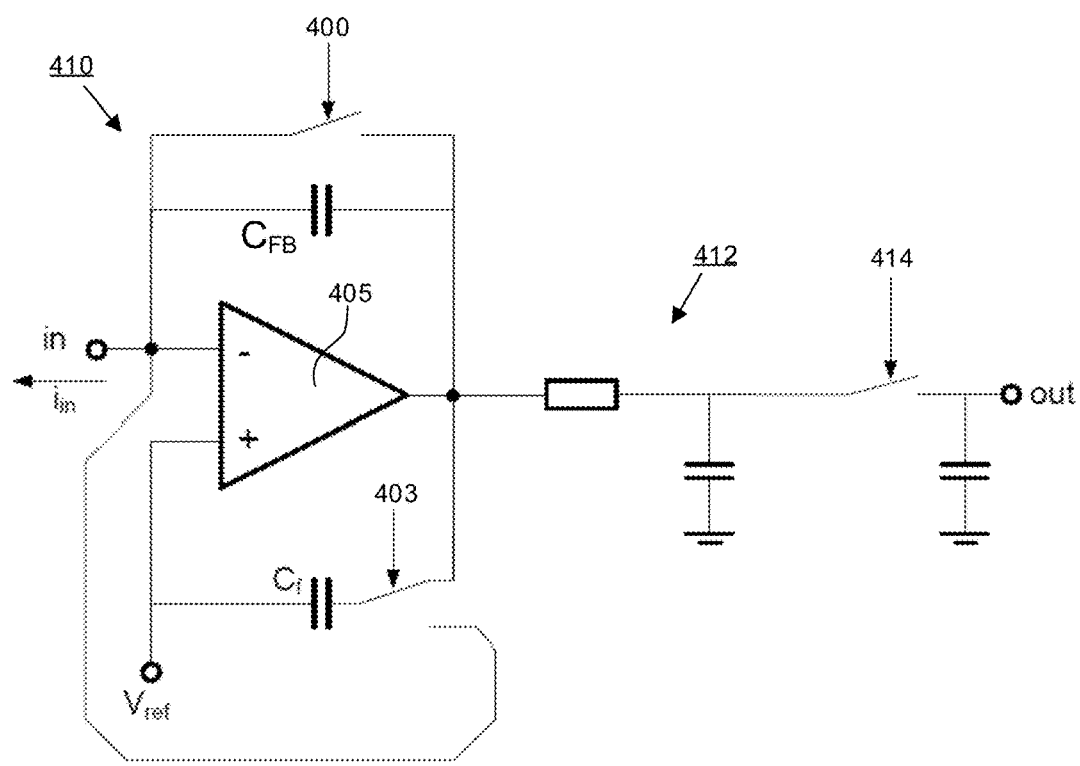
FIG. 24 depicts a test circuit for selectively implementing a hard reset mode and a charge balancing soft reset mode.
Figure 25:
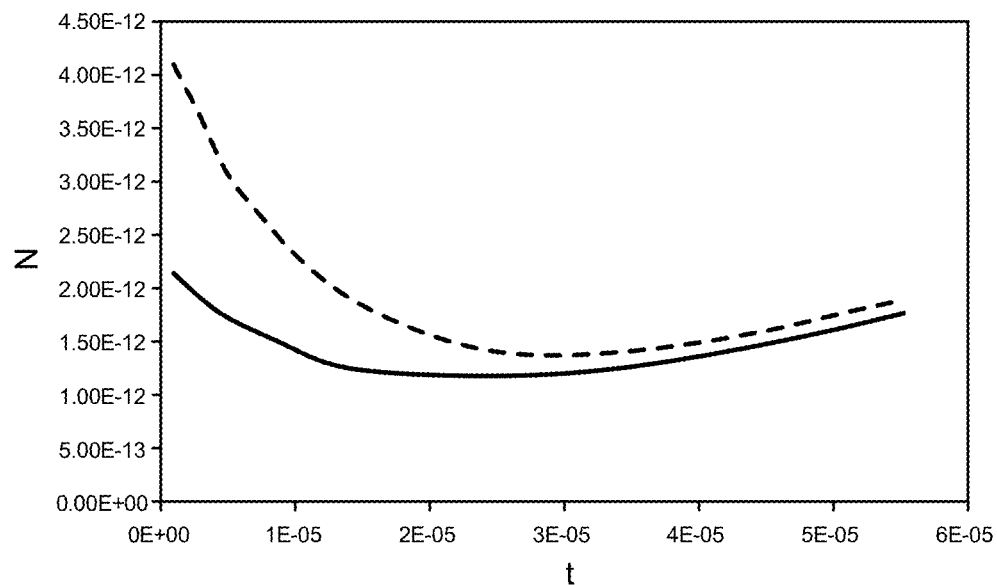
FIG. 25 is a graph comparing noise for the two reset modes obtained using the test circuit of FIG. 24.

FIG. 24 depicts a test circuit capable of implementing both the hard reset mode described above with reference to FIGS. 19-21 and the charge balancing soft reset mode. It is possible to select between the two modes to allow comparison. The noise spectral density of the OpAmp 405 behaves as 1/f at frequencies of interest, e.g. f<1/T with T the integration interval (size of the sensing frame). In a test experiment, the charge amplifier 410 was evaluated using T=100 μs integration intervals while a low-pass filter 412 was operated at a 10 kHz corner frequency. The timing of a CDS high-pass filter was programmable and defined by signal 414. Measurement results of the input-referred noise current (vertical axis) are shown in FIG. 25 as a function of time from the reset signal 400 to the CDS signal 414. The solid line shows variation of noise for the charge balancing soft reset mode. The broken line shows variation of noise for the hard reset mode. The charge balancing soft reset mode achieves lower circuit noise under all circumstances. The minimum noise was reduced by about 15%. The impact of low-frequency noise is most apparent shortly after the reset action, where up to a factor of two lower noise is achieved.

The current measuring apparatus described above with reference to FIG. 8 decreases power requirements by reducing the number of amplifiers needed to implement the current measuring functionality. However, the large number of components required to implement the circuit mean that considerable silicon area is needed. The current measuring apparatus described above with reference to FIG. 10 reduces the amount of silicon area that is needed for implementation by reducing the number of resistors and capacitors needed for the low pass filter modules. In the section above, a charge balanced soft reset mechanism was disclosed for enabling low noise current detection in combination with an RC filter and correlated double sampling.

A challenge with all of these methods is that the circuitry used for implementation must have sufficient speed, which may be achieved by providing appropriate amplifier bandwidth and bias current. When timings such as those depicted in FIG. 11 are used, for example, circuits need to settle to their operating points in time periods that are much shorter than the sensing frame e.g. by up to a factor 100. Providing high amplifier bandwidth and bias current can lead to higher power requirements and higher noise (due to the wider bandwidth).

Embodiments are described below which make use of the charge balancing soft reset mechanism described above to create a low power circuit by removing the need for circuit settling in a reset period and circuit settling for correlated double sampling. Then for each sensing frame only one sample is required (as opposed to two for correlated double sampling, one at the beginning of the sensing frame and one at the end of the sensing frame). This approach means the amplifiers involved can take all of the sensing frame to settle rather than up to 100th of the sensing frame. This means the amplifier bandwidth and bias current can be reduced significantly. This reduces power consumption. Low noise is also maintained. The circuitry needed to implement this approach is simple and makes little addition to the silicon area requirements.

The principle of charge balancing (which may also be referred to as charge feedback), as described above with reference to FIGS. 19-25, involves sampling of an output of a charge amplifier and feeding back of the sampled output to the input at regular intervals to bring the output back to a reset level. In principle this compensates for the switched component of noise.

However, the resetting of the charge amplifier causes noise folding. Under normal reset conditions the charge amplifier is a buffer with gain of 1 out to its unity-gain bandwidth. Now consider noise frequencies well beyond the sampling rate (e.g. 10 MHz when the sampling rate is 10 kHz). The noise is sampled in buffer mode and sees full gain of 1 as the charge amplifier is below the unity gain bandwidth. Then when coming out of reset to inverting charge amplifier mode the charge amplifier sees the gain given by the ratio of the capacitance at the input to the charge amplifier (e.g. a capacitance of an amphiphilic membrane when the apparatus is being used to measure current associated with a nanopore) to the integrating capacitance $C_{FB}$ (see FIG. 19 for example), e.g. 30 to 300, but it takes a few micro seconds to achieve this (i.e. the noise is been folded back to low frequencies). As most of the noise is at high frequencies this effect is large and results in a large switched component of noise, much larger than the continuous noise in charge mode. In charge reset mode the charge amplifier is always in inverting charge amplification mode. Therefore at high frequencies the gain is not seen due to the amplifier characteristics (see above). When charge balancing is used the noise folding sees a lower gain caused by the charge amplifier characteristic. This means the switched component of noise is considerably lower. This improvement is seen no matter what the unity gain bandwidth of the amplifier is (assuming a single pole amplifier characteristic).

Figure 26:
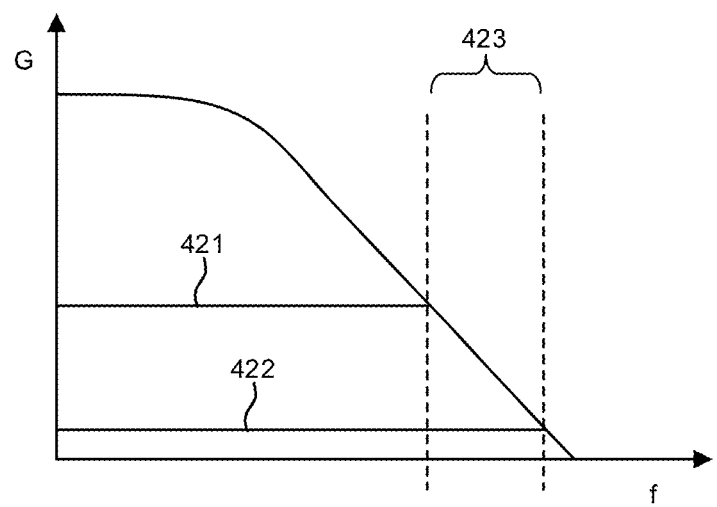
FIG. 26 is a schematic graph illustrated how switching noise is reduced using the charge balancing soft reset mode.

FIG. 26 is a graph of gain G against frequency schematically showing these concepts, wherein 421 indicates charge gain, 422 indicates unity gain, and the reduced gain from the amplifier is indicated by 423 (i.e. the noise sees the lower gain corresponding to the curve 422 rather than the gain of curve 421 and therefore has a lower impact). Analysing the noise (in a simplified manner for illustrative purposes), it is seen that for a normally reset operational mode the noise from the charge amplifier in the time domain can be characterized into two parts: a continuous component of noise Vn and a switched component of noise Vns. The comb and rectfunctions apply because the system is reset for a short period and as the circuit is released we have a sampled noise value that changes every sensing frame. Therefore the comb function samples a noise value Vns once every sensing frame and the convolution with a rectangle function spreads this across an integrating period in the sensing frame. The integrating period may be referred to as Tint. Tint is a small amount less than a sample period Ts. A reset period Treset is short. Noise when the circuit is reset is assumed to be virtually zero as the Gain G is 1 (the charge amplifier is a unity gain buffer) whereas in integrating mode it is a large value (determined, for example, as described above, by a ratio of a capacitance of an amphiphilic membrane to an integrating capacitance $C_{FB}$). It is possible to evaluate the noise by Fourier transformation. If the amplifier characteristics are added in, it is seen that the continuous component of noise Vn has gain related to an integrator, whereas the switched component of noise has gain relating to a unity gain buffer, which then sees the gain G when the mode switches into charge integration mode and samples the noise from the buffer mode. The equations below show these steps with equations, where $C_{PORE}$ represents a capacitance of an amphiphilic membrane and $C_{FB}$ represents an integrating capacitance:

$$V_{OUT} = G[V_n + rect(t, T_{INT}) \otimes (-V_{ns} \cdot comb(t, T_S))]$$

$$G = 1 + C_{PORE}/C_{FB}$$

$$rect(t, T_{INT}) = \begin{cases} 1 & \text{when } |t| < T_{INT}/2 \\ 0 & \text{otherwise} \end{cases}$$

$$comb(t, T_S) = \sum_{n=-\infty}^{\infty} \delta(t - nT_S)$$

$$T_S = T_{INT} + T_{RESET}$$

Fourier transforming yields the following:

$$\tilde{V}_{OUT}(f) = G\frac{T_{INT}}{T_S}\tilde{V}_n(f) - G\frac{T_{INT}}{T_S}sinc(\pi f T_{INT})\sum_{k=-\infty}^{\infty}\tilde{V}_{ns}(f - k/T_S)$$

Adding in amplifier characteristics yields the following:

$$\tilde{V}_{OUT}(f) = G\frac{T_{INT}}{T_S}\frac{1}{1-G/A(f)}\tilde{V}_n(f) - G\frac{T_{INT}}{T_S}\frac{A(f)}{1+A(f)}\mathrm{sinc}(\pi f T_{INT})\sum_{k=-\infty}^{\infty}\tilde{V}_{ns}(f-k/T_S)$$

If the charge feedback mode is now considered, the system is always in charge integration mode so when the amplifier characteristics are added it is seen that the equations change slightly, but the effect is large.

$$V_{OUT} = G[V_n + \mathrm{rect}(t, T_{INT}) \otimes (V_{ns} \cdot \mathrm{comb}(t, T_S))]$$

$$G = 1 + C_{PORE}/C_{FB}$$

$$\mathrm{rect}(t, T_{INT}) = \begin{cases} 1 & \text{when } |t| < T_{INT}/2 \\ 0 & \text{otherwise} \end{cases}$$

$$\mathrm{comb}(t, T_S) = \sum_{n=-\infty}^{\infty} \delta(t - nT_S)$$

$$T_S = T_{INT} + T_{RESET}$$

Fourier transforming yields the following:

$$\tilde{V}_{OUT}(f) = G\frac{T_{INT}}{T_S}\tilde{V}_n(f) + G\frac{T_{INT}}{T_S}\mathrm{sinc}(\pi f T_{INT})\sum_{k=-\infty}^{\infty}\tilde{V}_{ns}(f-k/T_S)$$

Adding in amplifier characteristics yields the following:

$$\tilde{V}_{OUT}(f) = G\frac{T_{INT}}{T_S}\frac{1}{1-G/A(f)}\tilde{V}_n(f) +$$

$$G\frac{T_{INT}}{T_S}\frac{1}{1-G/A(f)}\mathrm{sinc}(\pi f T_{INT})\sum_{k=-\infty}^{\infty}\tilde{V}_{ns}(f-k/T_S)$$

If we take the ratio of the second terms which represent the switched component of noise then we see that the ratio is much larger than 1 for high frequencies, i.e. when A(f) is less than G. Therefore the charge balancing soft reset approach outperforms the normal hard reset approach by a large factor:

$$\frac{V_{RESET}}{V_{CHARGE}} = \frac{A(f)/(1+A(f))}{1-G/A(f)} \approx \frac{1}{1-G/A(f)}$$

Taking A(f) to have a single pole at frequency $f_0$ and integrating over all frequencies we find that the ratio becomes $$\sqrt{\int\left(\frac{V_{RESET}}{V_{CHARGE}}\right)^2 df} = \pi\sqrt{f_0 A_0/G}$$

Note that with correlated double sampling the switched component of noise seen in the circuits is a residual effect due to non-perfect correlated double sampling. Therefore correlated double sampling also provides large reductions in switched noise. The point is that correlated double sampling can be avoided with the change balancing soft reset approach because this method alone gives a large reduction in switched noise.

Thus, in summary, a circuit is provided without correlated double sampling that produces low noise and does not need a hard reset. The issues with previous circuits have thus been removed and a single sampled circuit can be created which has very low power and good noise performance.

Furthermore the circuits of embodiments of the type depicted above with reference to FIGS. 8 and 10 require relatively large passive components (e.g. capacitors). The charge balancing soft reset approach can be implemented using fewer components than either of the approaches corresponding to FIGS. 8 and 10 and the single sampling (per sensing frame) means less storage is required. Circuits based on the charge balancing soft reset approach canthus provide efficiencies in terms of silicon area required for implementation. These advantages are illustrated in the example embodiments shown below.

Any of the embodiments discussed above with reference to FIGS. 5-18 can be adapted to use the charge balancing soft reset approach instead of a hard reset, although particular benefits will be obtained in terms of saving power and silicon area requirements by avoiding use of correlated double sampling.

Examples are depicted in FIGS. 27-30. In embodiments implementing the charge balancing soft reset approach, the first charge amplifier 201 is configured such that the integration of the current is performed simultaneously across a first capacitive element 431 (which may correspond, for example, to the integrating capacitor referred to above as $C_{FB}$) and a second capacitive element 432. The resetting of the first charge amplifier 201 is then performed by allowing a charge stored on the second capacitive element 432 to flow onto and at least partially cancel a charge stored on the first capacitive element 431.

Figure 27:
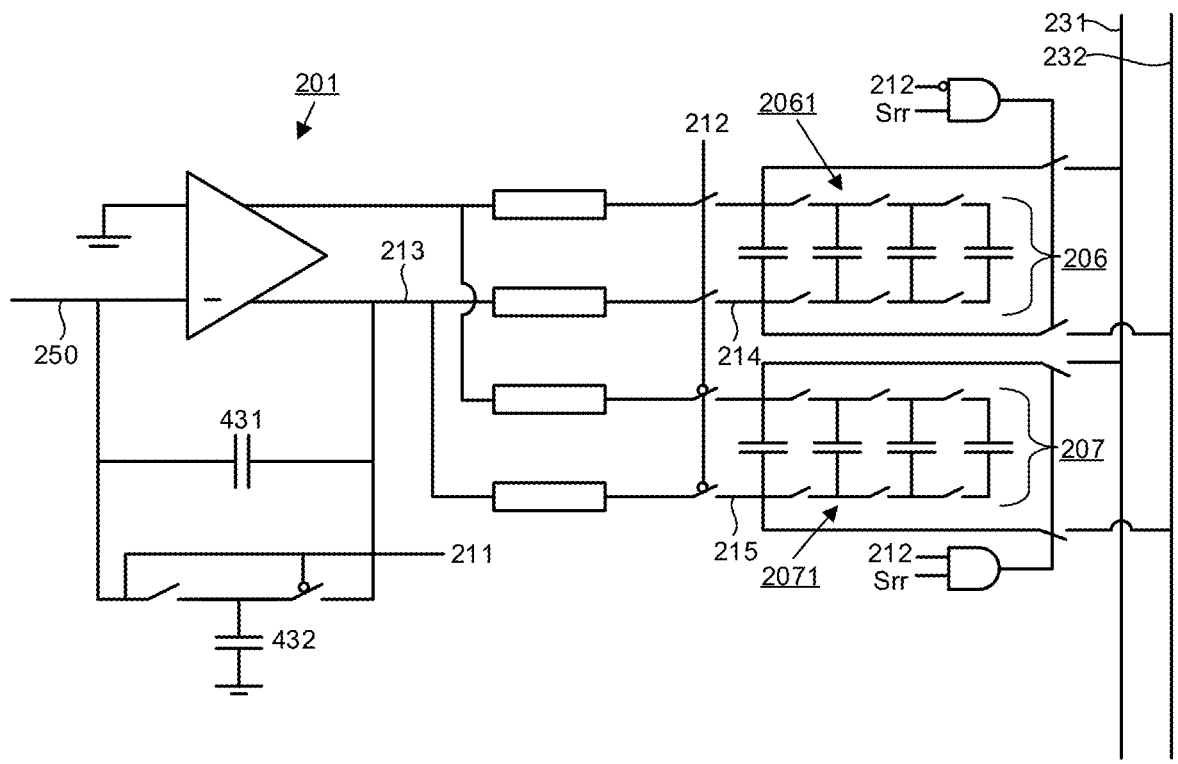
FIG. 27 depicts a portion of a current measuring apparatus corresponding to that of FIG. 8, adapted to use the charge balancing soft reset mode.
Figure 28:
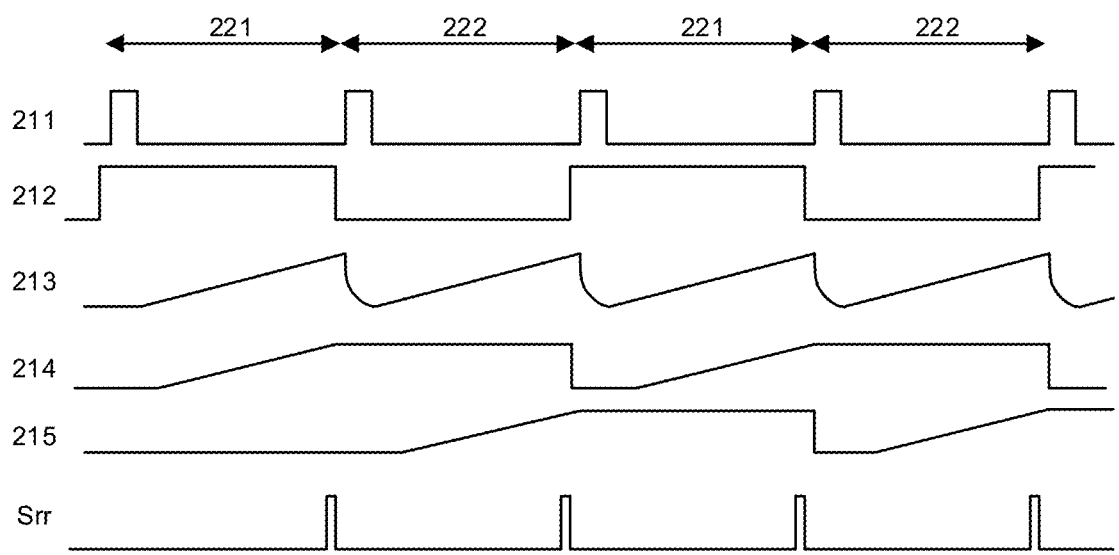
FIG. 28 depicts a timing diagram for operating the current measuring apparatus of FIG. 27.

FIG. 27 depicts an embodiment configured as in FIG. 5 described above, except that instead of the signal 211 driving a hard reset at a switch (as is the case in FIG. 5), the charge balancing soft reset approach is implemented instead. The timing diagram is shown in FIG. 28 and corresponds closely to the timing diagram of FIG. 7 (with corresponding elements having corresponding reference signs). The first charge amplifier 201 integrates the current to be measured simultaneously across a first capacitive element 431 (e.g. one or more capacitors) and a second capacitive element 432 (e.g. one of more capacitors). The resetting is performed then performed by allowing a charge stored on the second capacitive element 432 to flow onto and cancel a charge stored on the first capacitive element 431.

As described in detail with reference to FIG. 5, the first charge amplifier 201 is periodically reset by the reset signal 211, which defines a series of sensing frames 221 and 222. Sensing frames in which the flip signal 212 is predominantly high may be referred to as first sensing frames 221. Sensing frames in which the flip signal 212 is predominantly low may be referred to as second sensing frames 222. The first and second sensing frames 221 and 222 thus alternate in time. Sampling alternates between sampling via the first low pass filter module 206 and sampling via the second low pass filter module 207 to avoid the need for an RC filter buffer. The first low pass filter module 206 filters the first charge amplifier 201 output in each first sensing frame 221 and at the end of the first sensing frame 221 the a capacitor component of an RC filter of the first low pass filter module is isolated by the flip signal 212 to store the charge. In each second sensing frame 222, the second low pass filter module 207 filters the output of the first charge amplifier 201 and at the end of the second sensing frame 222 the charge is isolated by NOT flip signal 212 and stored. Also in each second sensing frame 222, the Srr signal activates (after an AND with the flip signal 212) output switches of the channel, thereby sending charge down the output lines 231 and 232 towards the second charge amplifier 202. The first and second pluralities of capacitors 2061 and 2071 are operated as described above with reference to FIG. 5 to allow a selected attenuation to be applied to the charge representing information about the current to be measured by reading out charge only from a selected subset of the first plurality of capacitors 2061 or the second plurality of capacitors 2071 (depending on which is being read out from).

When the reset signal 211 goes high charge in the second capacitive element 432 is forced into the input terminal of the first charge amplifier 201. The first charge amplifier 201 is forced to remove this charge by sending the opposite charge through the first capacitive element 431. This bring the first charge amplifier 201 back to its centre point which is effectively a reset of the first charge amplifier 201. Once all of the charge in the first capacitive element 431 is removed the reset signal 211 can go high once more so that the output of the first charge amplifier 201 can re-charge the first capacitive element 431. Therefore the reset period is effectively zero and the whole of the integration period is free to integrate current, which is not the case when a hard reset is performed by using a switch directly across the integrating capacitor (as in FIG. 5 for example). This approach increases the amount of time available to achieve maximum signal and thereby achieve low input referred current noise. This effect is in addition to the effects promoting low noise discussed above, with reference to FIG. 26 for example.

Figure 29:
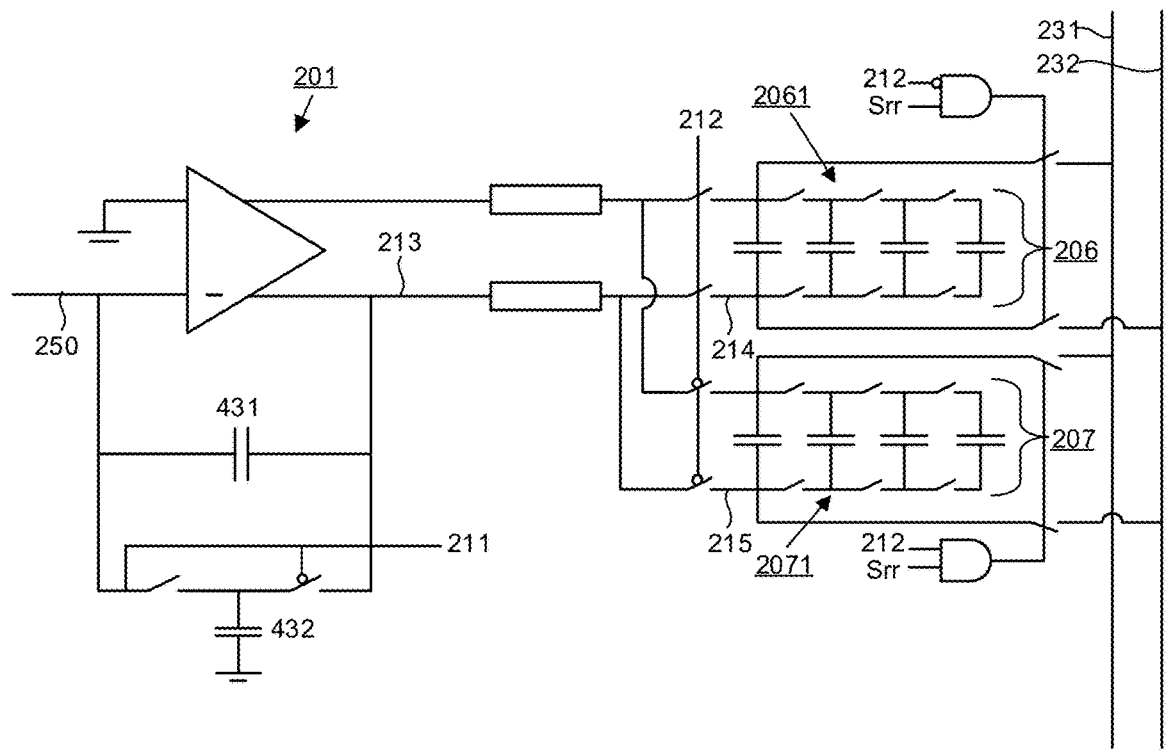
FIG. 29 depicts a variation on the arrangement of FIG. 27 in which only a single pair of resistor elements are used rather than two pairs of resistor elements to implement the two low pass filter modules.

FIG. 29 depicts a variation on the arrangement of FIG. 27 in which only a single pair of resistor elements are used rather than two pairs of resistor elements to implement the two low pass filter modules 206 and 207. The same timing is used (as depicted in FIG. 28) but the connection to the capacitors is now after the resistors (to the right of the resistors in the orientation of FIG. 29) rather than just after the first charge amplifier 201 (to the left of the resistors in the orientation of FIG. 29). Reducing the number of components needed reduces silicon area requirements.

Figure 30:
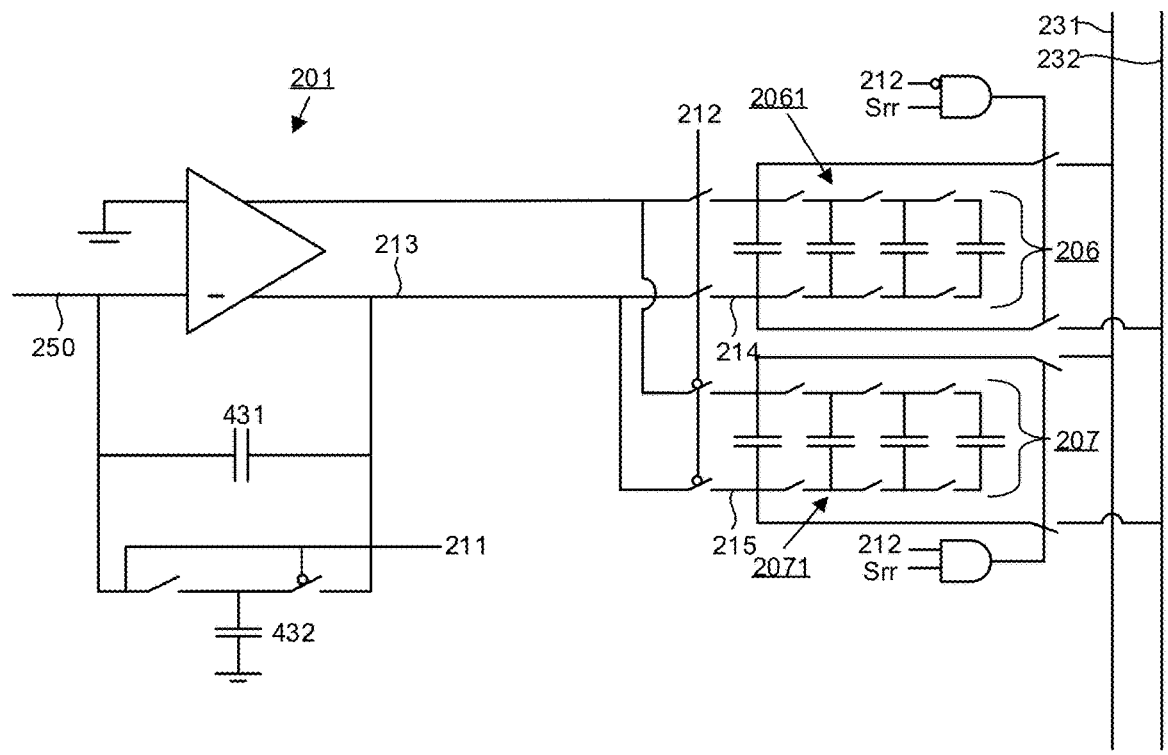
FIG. 30 depicts a variation on the arrangements of FIGS. 27 and 29 in which no separate resistor elements are used to implement the two low pass filter modules.

FIG. 30 depicts a further variation in which the bandwidth of the first charge amplifier 201 is arranged to be so low that the differential resistance component is no longer required, i.e. the output impedance of the first charge amplifier 201 provides the filtering of the signal in combination with the capacitors. This further reduces silicon area requirements.

Figure 31:
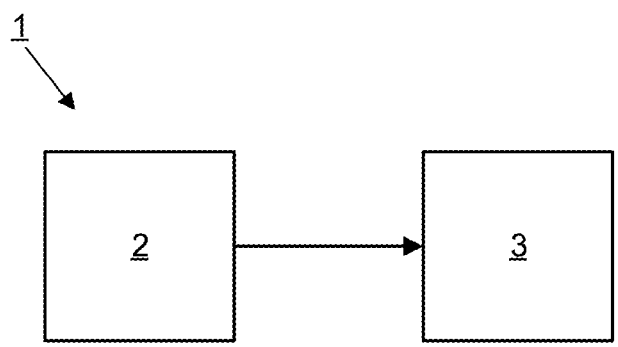
FIG. 31 depicts a molecular sensing apparatus.

The embodiments described above are fully differential in nature. The single ended versions of the circuits could be implemented as a matter of routine based on the teaching above and would provide similar advantages. The single ended versions may typically have lower performance in terms of signal dynamic range and noise, but they may benefit from lower power requirements as no common mode feedback circuitry is needed within the amplifiers. One or more of the current measuring apparatuses described above may be used in a molecular entity sensing apparatus 1, as depicted schematically in FIG. 31. The sensing apparatus 1 comprises a sensor device 2 and a detection circuit 3. In an embodiment, the sensor device 2 comprises an array of sensor elements 56 (see FIG. 32). In an embodiment, the detection circuit 3 comprises a plurality of current measuring apparatuses according to any of the embodiments disclosed above. Each current measuring apparatus measures the electrical current output by one or more of the sensor elements 56 and provides an output (e.g. a digital output) that is dependent on the current output by the one or more of the sensor elements 56.

In an embodiment, each of the sensor elements 56 comprises an ion channel. In an embodiment, the ion channel comprises a nanopore. In an embodiment, the ion channel comprises a membrane protein. In an embodiment, the sensor elements 56 are each arranged to support an amphiphilic membrane in which a membrane protein is capable of insertion. The interaction between the molecular entity and the sensor element 56 is in this case an interaction between the molecular entity and the membrane protein in the amphiphilic membrane.

Figure 32:
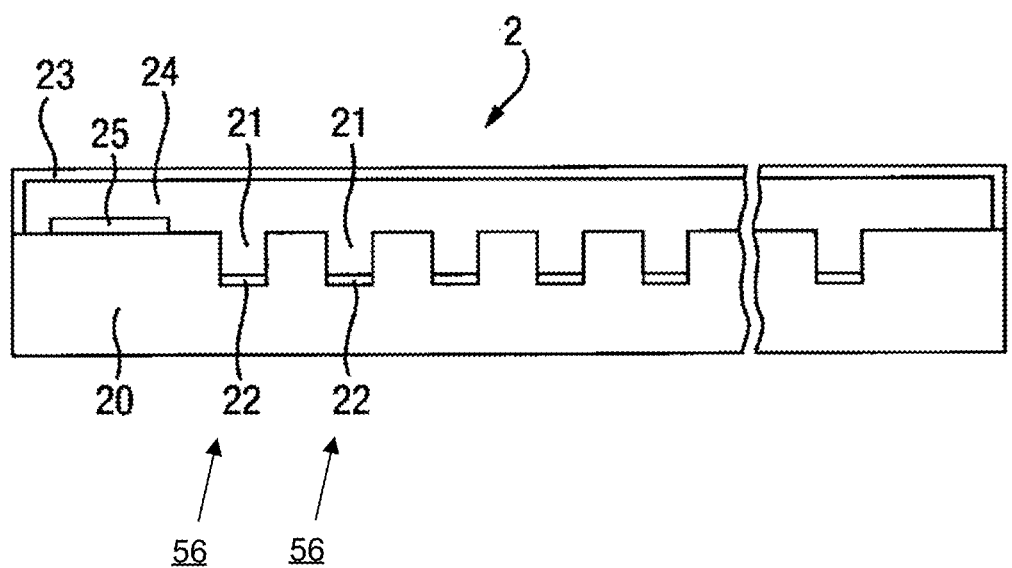
FIG. 32 depicts an example sensor device of the molecular sensing apparatus of FIG. 31.

In an embodiment the sensor device 2 is an apparatus as described in detail in US2011/0120871A1 which is incorporated herein by reference. Without limitation to the generality of the teaching therein, the sensor device 2 of this type has a construction as shown in cross-section in FIG. 32 comprising a body 20 in which there is formed a plurality of wells 21 each being a recess having a well electrode 22 arranged therein. A large number of wells 21 is provided to optimise the data collection rate of the apparatus 1. In general, there may be any number of wells 21, typically 256 or 1024, although only a few of the wells 21 are shown in FIG. 32. Each well 21 and corresponding well electrode 22 is an example of a sensor element 56.

In this embodiment the body 20 is covered by a cover 23 that extends over the body 20 and is hollow to define a chamber 24 into which each of the wells 21 opens. A common electrode 25 is disposed within the chamber 23. Each sensor element 56 is arranged to output an electrical current that is dependent on an interaction between a molecular entity and the sensor element 56, as described with reference to exemplary configurations below.

In the embodiment shown, the sensor device 2 is prepared to form an amphiphilic membrane across each well 21 and to insert membrane proteins into the amphiphilic membrane. This preparation may be achieved using the techniques and materials described in detail in US2011/0120871A1, which may be summarised as follows. Aqueous solution is introduced into the chamber 24 to form the amphiphilic membrane across each well 21 separating aqueous solution in the well 21 from the remaining volume of aqueous solution in the chamber 24. Membrane proteins are provided into the aqueous solution, for example by being introduced into the aqueous solution before or after that is introduced into the chamber 24 or by being deposited on an internal surface of the chamber 24. The membrane proteins spontaneously insert from the aqueous solution into the amphiphilic membranes. Such spontaneous insertion is a dynamic process and so there is a statistical variation in the number of membrane proteins inserted into individual amphiphilic membranes, typically having a Poisson distribution. Other sensor devices suitable for use in the invention are disclosed in WO2014064449A1.

In respect of any given well 21, when an amphiphilic membrane has been formed and a membrane protein is inserted therein, then the well 21 is capable of being used as part of a sensor element 56 that is configured to sense interactions between molecular entities and the membrane protein. These interactions are stochastic physical events. The output electrical signal across the amphiphilic membrane is dependent on the interactions in the sense that the interactions cause characteristic changes in the output electrical signal. For example in the case that the membrane protein is a protein pore, then there will typically be interactions between the protein pore and a particular molecular entity (analyte) that modulate the flow of ions through the pore. The modulation of the flow of ions through the pore creates a characteristic change in current flow through the pore. The molecular entity may be a molecule or part of a molecule, for example a DNA base. Such interactions are typically very brief, requiring a high time resolution and continuous monitoring if it is desired to detect each interaction.

Any membrane may be used in accordance with various aspects described herein. Suitable membranes are well-known in the art. The membrane can be an amphiphilic layer or a solid-state layer. An amphiphilic layer is a layer formed from amphiphilic molecules, such as phospholipids, which have both hydrophilic and lipophilic properties. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). The copolymer May 30 be a triblock, tetrablock or pentablock copolymer. The membrane can be a triblock or diblock copolymer membrane.

Membranes formed from block copolymers hold several advantages over biological lipid membranes. Because the triblock copolymer is synthesized, the exact construction can be carefully controlled to provide the correct chain lengths and properties required to form membranes and to interact with pores and other proteins.

Block copolymers may also be constructed from sub-units that are not classed as lipid sub-materials; for example, a hydrophobic polymer may be made from siloxane or other non-hydrocarbon-based monomers. The hydrophilic sub-section of block copolymer can also possess low protein binding properties, which allows the creation of a membrane that is highly resistant when exposed to raw biological samples. This head group unit may also be derived from non-classical lipid head-groups.

Triblock copolymer membranes also have increased mechanical and environmental stability compared with biological lipid membranes, for example a much higher operational temperature or pH range. The synthetic nature of the block copolymers provides a platform to customize polymer-based membranes for a wide range of applications.

The membrane can be one of the membranes disclosed in US2015/0265994A1 or US2015/0285781A1 hereby incorporated by reference in its entirety. These documents also disclose suitable polymers.

The amphiphilic molecules may be chemically-modified or functionalized to facilitate coupling of the polynucleotide. The amphiphilic layer may be a monolayer or a bilayer. The amphiphilic layer is typically planar. The amphiphilic layer may be curved. The amphiphilic layer may be supported. The amphiphilic layer may be concave. The amphiphilic layer may be suspended from raised pillars such that the peripheral region of the amphiphilic layer (which is attached to the pillars) is higher than the amphiphilic layer region. This may allow the microparticle to travel, move, slide or roll along the membrane as described above.

The membrane may be a lipid bilayer. Suitable lipid bilayers are disclosed in WO2008/102121, WO 2009/077734 and WO 2006/100484.

Methods for forming lipid bilayers are known in the art. Lipid bilayers are commonly formed by the method of Montal and Mueller (Proc. Natl. Acad. Sci. USA., 1972; 69:3561-3566), in which a lipid monolayer is carried on aqueous solution/air interface past either side of an aperture which is perpendicular to that interface.

Solid state layers can be formed from both organic and inorganic materials including, but not limited to, microelectronic materials, insulating materials such as $Si_3N_4$, $Al_2O_3$, and $SiO$, organic and inorganic polymers such as polyamide, plastics such as Teflon® or elastomers such as two-component addition-cure silicone rubber, and glasses. The solid-state layer may be formed from graphene. Suitable graphene layers are disclosed in WO 2009/035647. Yusko et al., Nature Nanotechnology, 2011; 6:253-260 and US Patent Application No. 2013/0048499 describe the delivery of proteins to transmembrane pores in solid state layers without the use of microparticles.

Any transmembrane pore may be used. The pore may be biological or artificial. Suitable pores include, but are not limited to, protein pores, polynucleotide pores and solid-state pores. The pore may be a DNA origami pore (Langecker et al., Science, 2012; 338:932-936).

The transmembrane pore can be a transmembrane protein pore. A transmembrane protein pore is a polypeptide or a collection of polypeptides that permits hydrated ions, such as the by-products of processing a polynucleotide with a polymerase, to flow from one side of a membrane to the other side of the membrane. In one embodiment, the transmembrane protein pore is capable of forming a pore that permits hydrated ions driven by an applied potential to flow from one side of the membrane to the other. The transmembrane protein pore can permit polynucleotides to flow from one side of the membrane, such as a triblock copolymer membrane, to the other. The transmembrane protein pore may allow a polynucleotide, such as DNA or RNA, to be moved through the pore.

The transmembrane protein pore may be a monomer or an oligomer. The pore can be made up of several repeating subunits, such as at least 6, at least 7, at least 8, at least 9, at least 10, at least 11, at least 12, at least 13, at least 14, at least 15, or at least 16 subunits. The pore can be a hexameric, heptameric, octameric or nonameric pore. The pore may be a homo-oligomer or a hetero-oligomer.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with nucleotides, polynucleotides or nucleic acids. These amino acids can be located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. The transmembrane pore may be derived from or based on Msp, α-hemolysin (α-HL), lysenin, CsgG, ClyA, Spl and hemolytic protein fragaceatoxin C (FraC). The transmembrane protein pore can be derived from CsgG. Suitable pores derived from CsgG are disclosed in WO 2016/034591. The transmembrane pore may be derived from lysenin. Suitable pores derived from lysenin are disclosed in WO 2013/153359.

The analytes (including, e.g., proteins, peptides, small molecules, polypeptide, polynucleotides) may be present in an analyte. The analyte may be any suitable sample. The analyte may be a biological sample. Any embodiment of the methods described herein may be carried out in vitro on an analyte obtained from or extracted from any organism or microorganism. The organism or microorganism is typically archaean, prokaryotic or eukaryotic and typically belongs to one of the five kingdoms: plantae, animalia, fungi, monera and protista. In some embodiments, the methods of various aspects described herein may be carried out in vitro on an analyte obtained from or extracted from any virus.

The analyte can be a fluid sample. The analyte can comprise a body fluid. The body fluid may be obtained from a human or animal. The human or animal may have, be suspected of having or be at risk of a disease. The analyte may be urine, lymph, saliva, mucus, seminal fluid or amniotic fluid, but can be whole blood, plasma or serum. Typically, the analyte is human in origin, but alternatively it may be from another mammal such as from commercially farmed animals such as horses, cattle, sheep or pigs or may alternatively be pets such as cats or dogs.

Alternatively, an analyte can be of plant origin.

The analyte may be a non-biological sample. The non-biological sample can be a fluid sample. An ionic salt such as potassium chloride may be added to the sample to effect ion flowthrough the nanopore.

The polynucleotide may be single stranded or double stranded. At least a portion of the polynucleotide may be double stranded.

The polynucleotide can be a nucleic acid, such as deoxyribonucleic acid (DNA) or ribonucleic acid (RNA). The polynucleotide can comprise one strand of RNA hybridised to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. The polynucleotide can be any length.

Any number of polynucleotides can be investigated. For instance, the method may concern characterising 2, 3, 4, 5, 6, 7, 8, 9, 10, 20, 30, 50, 100 or more polynucleotides. If two or more polynucleotides are characterised, they may be different polynucleotides or two instances of the same polynucleotide.

The polynucleotide can be naturally occurring or artificial.

The method may involve measuring two, three, four or five or more characteristics of a polynucleotide. The one or more characteristics can be selected from (i) the length of the polynucleotide, (ii) the identity of the polynucleotide, (iii) the sequence of the polynucleotide, (iv) the secondary structure of the polynucleotide and (v) whether or not the polynucleotide is modified.

For (iii), the sequence of the polynucleotide can be determined as described previously. Suitable sequencing methods, particularly those using electrical measurements, are described in Stoddart D et al., Proc Natl Acad Sci, 12; 106 (19): 7702-7, Lieberman K R et al, J Am Chem Soc. 2010; 132 (50): 17961-72, and International Application WO 2000/28312.

The secondary structure may be measured in a variety of ways. For instance, if the method involves an electrical measurement, the secondary structure may be measured using a change in dwell time or a change in ion current flowing through the pore. This allows regions of single-stranded and double-stranded polynucleotide to be distinguished.

The presence or absence of any modification may be measured. The method can comprises determining whether or not the polynucleotide is modified by methylation, by oxidation, by damage, with one or more proteins or with one or more labels, tags or spacers.

Specific modifications will result in specific interactions with the pore which can be measured using the methods described below.

In some embodiments of various aspects described herein, the method may involve further characterizing the target polynucleotide. As the target polynucleotide is contacted with the pore, one or more measurements which are indicative of one or more characteristics of the target polynucleotide are taken as the polynucleotide moves with respect to the pore.

The method may involve determining whether or not the polynucleotide is modified. The presence or absence of any modification may be measured. The method can comprises determining whether or not the polynucleotide is modified by methylation, by oxidation, by damage, with one or more proteins or with one or more labels, tags or spacers.

Also provided is a kit for characterising a target polynucleotide. The kit comprises a pore as disclosed herein and the components of a membrane. The membrane can be formed from the components. The pore can be present in the membrane. The kit may comprise components of any of the membranes disclosed above, such as an amphiphilic layer or a triblock copolymer membrane.

Also provided is an apparatus for characterising a target analyte, such as a target polynucleotide. The apparatus comprises a plurality of the pores as disclosed herein and a plurality of membranes. The plurality of pores can be present in the plurality of membranes. The number of pores and membranes can be equal. A single pore can be present in each membrane.

The apparatus for characterising target analytes, may comprise or an array of pores as disclosed herein, in a plurality of membranes.

The apparatus can further comprises instructions for carrying out the method. The apparatus may be any conventional apparatus for analyte analysis, such as an array or a chip. Any of the embodiments discussed above with reference to the methods are equally applicable to the apparatus of the invention. The apparatus may further comprise any of the features present in the kit as disclosed herein.

The apparatus can be set up to carry out a method as disclosed herein.

The apparatus can comprise: a sensor device that is capable of supporting the plurality of pores and membranes and being operable to perform analyte characterisation using the pores and membranes; and at least one port for delivery of the material for performing the characterisation.

Alternatively, the apparatus can comprise: a sensor device that is capable of supporting the plurality of pores and membranes being operable to perform analyte characterisation using the pores and membranes; and at least one reservoir for holding material for performing the characterisation.

The apparatus can comprise: a sensor device that is capable of supporting the membrane and plurality of pores and membranes and being operable to perform analyte characterising using the pores and membranes; at least one reservoir for holding material for performing the characterising; a fluidics system configured to controllably supply material from the at least one reservoir to the sensor device; and one or more containers for receiving respective samples, the fluidics system being configured to supply the analytes selectively from one or more containers to the sensor device.

The apparatus may be any of those described in WO 2009/077734, WO 2010/122293, WO 2011/067559 or WO 00/28312.

Control of the movement of an analyte with respect to the nanopore e.g. speed of translocation, rejection of the analyte etc, can be managed by the systems and methods disclosed in US2017/0233804A1, incorporated herein by reference in its entirety. Rejection of an analyte by the nanopore sensor can comprise ejection of the analyte from the nanopore.

The features in description above and in Figures of the invention are interchangeable and compatible in light of the teaching herein. The present invention has been described above purely by way of example, and modifications can be made within the spirit and scope of the invention, which extends to equivalents of the features described and combinations of one or more features described herein. The invention also consists in any individual features described or implicit herein.

The invention claimed is:

1. A method of measuring current, comprising:
using a first charge amplifier to integrate a current to be measured;
filtering an output from the first charge amplifier using a first low pass filter module and a second low pass filter module; and
using a second charge amplifier to integrate a current derived from the filtered output from the first charge amplifier, wherein:
the first charge amplifier is reset at the start of each of a plurality of sensing frames;
at least a first sample of the output from the first charge amplifier is obtained in each sensing frame; and
the sampling of the first sample alternates from one sensing frame to the next sensing frame between sampling via the first low pass filter module and sampling via the second low pass filter module.

2. A method of sensing a molecular entity, comprising using the method of claim 1 to measure an electrical current that is dependent on an interaction between a molecular entity and a sensor element.

3. The method of claim 2, wherein each of the sensor elements comprises a nanopore.

4. The method of claim 1, wherein the first low pass filter module comprises a first RC filter and the second low pass filter module comprises a second RC filter.

5. The method of claim 4, wherein either or both of the following conditions is/are satisfied:
in each sensing frame in which sampling of a first sample is not performed via the firstlow pass filter module, a first sample from a directly preceding sensing frame is stored as charge on a capacitance component of the first RC filter; and
in each sensing frame in which sampling of the first sample is not performed via the second low pass filter module, a first sample from a directly preceding sensing frame is stored as charge on a capacitance component of the second RC filter.

6. The method of claim 4, wherein either or both of the following conditions is satisfied:
the capacitance component of the first RC filter comprises a first plurality of capacitors and in each sensing frame in which sampling of the first sample is performed via the first low pass filter module, a selected attenuation is applied to charge representing information about the current to be measured by sampling charge only from a selected subset of the first plurality of capacitors; and
the capacitance component of the second RC filter comprises a second plurality of capacitors and in each sensing frame in which sampling of the first sample is performed via the second low pass filter module, a selected attenuation is applied to charge representing information about the current to be measured by sampling charge only from a selected subset of the second plurality of capacitors.

7. The method of claim 1, wherein the first sample and a second sample of the output from the first charge amplifier are obtained in each sensing frame and the processing circuit is configured to perform correlated double sampling using the first sample and second sample.

8. The method of claim 7, wherein the sampling of the second sample alternates from one sensing frame to the next sensing frame between sampling via a third low pass filter module and sampling via a fourth low pass filter module.

9. The method of claim 7, wherein a difference between the first sample and the second sample in each sensing frame is implemented by combining with reversed polarities an output from the low pass filter module that stores charge corresponding to the first sample and an output from the low pass filter module that stores charge corresponding to the second sample.

10. The method of claim 1, wherein each of the first low pass filter module, the second low pass filter module, and a further low pass filter module is reset in each sensing frame in which the respective low pass filter module obtains a sample.

11. The method of claim 10, wherein the resetting of each low pass filter module is performed by bypassing a resistance component of an RC filter of the low pass filter module.

12. The method of claim 10, wherein the timing of the resetting of each low pass filter module is such that each of the first sample and the second sample is obtained an equal time after the resetting of the low pass filter module via which the sample is sampled.

13. The method of claim 1, wherein the integration of the current is performed simultaneously across a first capacitive element and a second capacitive element, and the resetting of the first charge amplifier is performed by allowing a charge stored on the second capacitive element to flow onto and at least partially cancel a charge stored on the first capacitive element.

14. A method of measuring current, comprising:
using a first charge amplifier to integrate a current to be measured;
filtering an output from the first charge amplifier; and
using a second charge amplifier to integrate a current derived from the filtered output from the first charge amplifier, wherein:
the integration of the current by the first charge amplifier is performed simultaneously across a first capacitive element and a second capacitive element and the resetting of the first charge amplifier is performed by allowing a charge stored on the second capacitive element to flow onto and at least partially cancel a charge stored on the first capacitive element.

15. A method of measuring current, comprising:
using a first charge amplifier to integrate a current to be measured;
using a processing circuit to filter an output from the first charge amplifier; and using a second charge amplifier to integrate a current derived from the filtered output from the first charge amplifier, wherein:

the processing circuit is configured such that information about the current to be measured propagates through the processing circuit from the first charge amplifier to the second charge amplifier as amounts of charge representing the current to be measured.

16. The method of claim 15, wherein the processing circuit exclusively consists of passive components and externally controllable switches.

* * * * *